(12) United States Patent
Krakover et al.

(10) Patent No.: US 6,458,273 B1
(45) Date of Patent: Oct. 1, 2002

(54) SAMPLE SEPARATION APPARATUS AND METHOD FOR MULTIPLE CHANNEL HIGH THROUGHPUT PURIFICATION

(75) Inventors: Jonathan D. Krakover, Vista; Romaine Maiefski, Ocean Side, both of CA (US)

(73) Assignee: Ontogen Corporation, Carlsbad, CA (US)

( * ) Notice: Subject to any disclaimer, the term of this patent is extended or adjusted under 35 U.S.C. 154(b) by 0 days.

(21) Appl. No.: 09/569,378

(22) Filed: May 11, 2000

Related U.S. Application Data

(63) Continuation-in-part of application No. 09/430,194, filed on Oct. 29, 1999, now Pat. No. 6,309,541.

(51) Int. Cl.$^7$ .............................................. B01D 15/08
(52) U.S. Cl. ..................... 210/198.2; 210/656; 210/659
(58) Field of Search ................................. 210/635, 656, 210/659, 143, 198.2; 95/82, 86; 96/101, 104; 422/70; 436/161

(56) References Cited

U.S. PATENT DOCUMENTS

| | | | |
|---|---|---|---|
| 2,733,135 A | 1/1956 | Huckabay ................. | 210/198.2 |
| 3,250,395 A | 5/1966 | Blume ......................... | 210/263 |
| 4,079,009 A | 3/1978 | Seiler et al. ............. | 210/198.2 |
| 4,554,071 A | 11/1985 | Ruijten et al. ........... | 210/198.2 |
| 4,719,011 A | 1/1988 | Shalon et al. ............ | 210/198.2 |
| 4,766,082 A | 8/1988 | Marteau D'Autry ........ | 436/178 |
| 4,787,971 A | 11/1988 | Donald .................... | 210/198.2 |
| 5,009,778 A | 4/1991 | Nickerson et al. ....... | 210/198.2 |
| 5,151,178 A | 9/1992 | Nickerson et al. ....... | 210/198.2 |
| 5,234,599 A | 8/1993 | Cortes et al. ............ | 210/198.2 |
| 5,614,089 A | 3/1997 | Allington et al. ........ | 210/198.2 |
| 5,670,054 A | 9/1997 | Kibbey et al. ........... | 210/198.2 |
| 5,766,460 A * | 6/1998 | Bergstrom ............... | 210/198.2 |

(List continued on next page.)

FOREIGN PATENT DOCUMENTS

| | | | |
|---|---|---|---|
| SU | 940057 | 6/1982 | .............. 210/198.2 |
| WO | WO98/35227 | 8/1998 | .............. 210/198.2 |

OTHER PUBLICATIONS

E. Von Arx, P. Richert, R. Stoll, K. Wagner, and Wuest, "New Aids for Preparative High–Performance Liquid Chromatography", Journal of Chromatography, 1982, vol. 238, pp. 419–425.

Michael J. Kessler, "Quantitation of Radiolabeled Biological Molecules Separated by High–Performance Liquid Chromatography", Journal of Chromatography, 1983, vol. 255, pp. 209–217.

Robert M. Campbell and Milton L. Lee, "Supercritical Fluid Fractionation of Petroleum– and Coal–Derived Mixtures", Anal. Chem., 1986, vol. 58, No. 11, pp. 2247–2251.

(List continued on next page.)

*Primary Examiner*—Ernest G. Therkorn
(74) *Attorney, Agent, or Firm*—Perkins Coie LLP

(57) ABSTRACT

A high throughput liquid chromotagraphy column assembly for separating a large sample with a selected mass weight and fluid volume. The assembly includes a loading column with a loading chamber with a first inner diameter and a first length. The loading chamber contains a packing material on to which sample is loaded and spatially distributed. The length of the loading chamber's volume is sufficient to fully load the sample therein but the length of the loading chamber is insufficient to achieve the selected chromotagraphic separation. A separation column is in fluid communication with the loading column. The separation column has a separation chamber with a diameter smaller than the loading column's inner diameter and a length greater than the loading column's length. In one embodiment, the loading column has a diameter two or more times greater than the separation chamber's diameter, and the loading column has a length one-half or less than the length of the separation chamber. The separation chamber's diameter is such that the separation chamber has a volume over the same length as the loading column's length that is insufficient to act as a loading area for the entire selected sample for the given mass and volume of the sample.

34 Claims, 28 Drawing Sheets

U.S. PATENT DOCUMENTS

| | | | | |
|---|---|---|---|---|
| 5,863,428 A | * | 1/1999 | Ma | 210/198.2 |
| 5,938,932 A | | 8/1999 | Connelly et al. | 210/198.2 |
| 6,054,047 A | | 4/2000 | Hindsgaul et al. | 210/198.2 |
| 6,080,318 A | | 6/2000 | Gumm et al. | 210/659 |
| 6,090,280 A | | 7/2000 | Connelly et al. | 210/198.2 |
| 6,197,198 B1 | | 3/2001 | Messinger et al. | 210/656 |
| 6,210,571 B1 | | 4/2001 | Zambias et al. | 210/198.2 |

OTHER PUBLICATIONS

Johan Uusijarvi, Borje Egestad, and Jan Sjovall, "Manual and Automated Enrichment Procedures for Biological Samples using Lipophilic Gels", Journal of Chromatography, 1989, vol. 488, pp. 87–104.

Tooru Imahashi, Yoshio Yamauchi, and Munco Saito, "Fractionation and Identification of Additives in Polyvinylchloride Film by Supercritical Fluid Extraction/Semi–Preparative Supercritical Fluid Chromatography", Bunseki Kagaku, 1990, vol. 39, pp. 79–85.

Hans M.H. van Eijk, Mark P.L. Huinck, Dennis R. Rooyakkers, and Nicolaas E.P. Deutz, "Automated Simultaneous Isolation and Quantitation of Labeled Amino Acid Fractions From Plasma and Tissue by Ion–Exchange Chromatography", Journal of Chromatography B, 1994, vol. 660, pp. 251–257.

John F. Cargill and Romaine R. Maiefski, "Automated Combinatorial Chemistry on Solid Phase", Laboratory Robotics and Automation, 1996, vol. 8, pp. 139–148.

Robert Pal, Kristina Tolvaj, and Miklos Juhasz, "Separation of Gas Oil Samples by Coupled Packed and Open Tubular Column SFC", J. Microcolumn Separations, 1996, vol. 8, pp. 269–273.

Bradley L. Ackermann and Brian T. Regg, "Rapid Analysis of Antibiotic–Containing Mixtures From Fermentation Broths by Using Liquid Chromatography–Electrospray Ionization–Mass Spectrometry and Matrix–Assisted Laser Desorption Ionization–Time–of–Flight–Mass Spectrometry", Journal of the American Society of Mass Spectrometry, 1996, vol. 7, pp. 1227–1237.

Donald J. Daley, Russel D. Scammell, David James, Iain Monks, Roberto Raso, Alison E. Ashcroft, and Aaron J. Hudson, "High–Throughput LC–MS Verification of Drug Candidates From 96–Well Plates", Am. Biotechnol. Lab., Nov. 1997, vol. 15, pp. 24, 26, and 28.

Christopher E. Kibbey, "An Automated System for the Purification of Combinatorial Libraries by Preparative LC/MS", Laboratory Robotics and Automation, 1997, vol. 9, pp. 309–321.

L. Zeng, L. Burton, K. Yung, B. Shushan, and D.B. Kassel, "Automated Analytical/Preparative High–Performance Liquid Chromatography–Mass Spectrometry System for the Rapid Characterization and Purification of Compound Libraries", Journal of Chromatography A, Jan. 23, 1998, vol. 794, Nos. 1 and 2, pp. 3–13.

Chemical Abstracts, vol. 128, No. 13, Mar. 30, 1998, Angelika Weber, Holger Theils, and Reza Hashemi, "Automated and Flexible Chromatographic Purification. Part 2. Experiences in the Operational Phase", p. 1320, col. 2, Abstract No. 162374p, LaborPraxis, 1998, 22(1), 43–44.

Chemical Abstracts, vol. 129, No. 7, Aug. 17, 1998, Jeffrey Kiplinger et al., "Structure–Controlled Automated Purification of Parallel Synthesis Products in Drug Discovery", p. 655, col. 2, Abstract No. 81293e, Rapic Commun. Mass Spectrom., 1998, 12(10), 658–664.

T. Wang, L. Zeng, T. Strader, L. Burton, and Daniel B. Kassel, "A New Ultra–High Throughput Method for Characterizing Combinatorial Libraries Incorporating a Multiple Probe Autosampler Coupled with Flow Injection Mass Spectrometry Analysis", Rapid Commun. Mass Spectrom., 1998, vol. 12, pp. 1123–1129.

Lu Zeng and Daniel B. Kassel, "Developments of a Fully Automated Parallel HPCL/Mass Spectrometry System for the Analytical Characterization and Preparative Purification of Combinatorial Libraries", Anal. Chem., 1998, vol. 70, pp. 4380–4388.

F. Vérillon, D. Heems, B. Pichon, K. Coleman, and J.–C Robert, "Supercritical fluid chromatography With Independent Programming of Mobile–Phase Pressure, Composition, and Flow Rate", American Laboratory, Jun. 1992, 8 pages.

M. Ashraf–Khorassani, M.B. Gandee, M.T. Combs, and L. T. Taylor, "Semipreparative Separation and Fractionation of Sulfonamides via Supercritical Fluid Chromatography", Journal of Chromatographic Science, vol. 35, Dec. 1997, pp. 593–597.

"Gilson Supercritical Fluid Chromatography", booklet reproducing chapter entitled "Analytical and Preparative Carbon Dioxide Chromatography with Automated Pressure Control and Different Detectors" by Francis Vérillon and Keith Coleman, from the Marcel Dekker, Inc. book entitled "Supercritical Fluid Chromatography with Packed Columns: Techniques and Applications", edited by Klaus Anton and Claire Berger, France, Reference 800347A, May 1998, pp. 1–49.

* cited by examiner

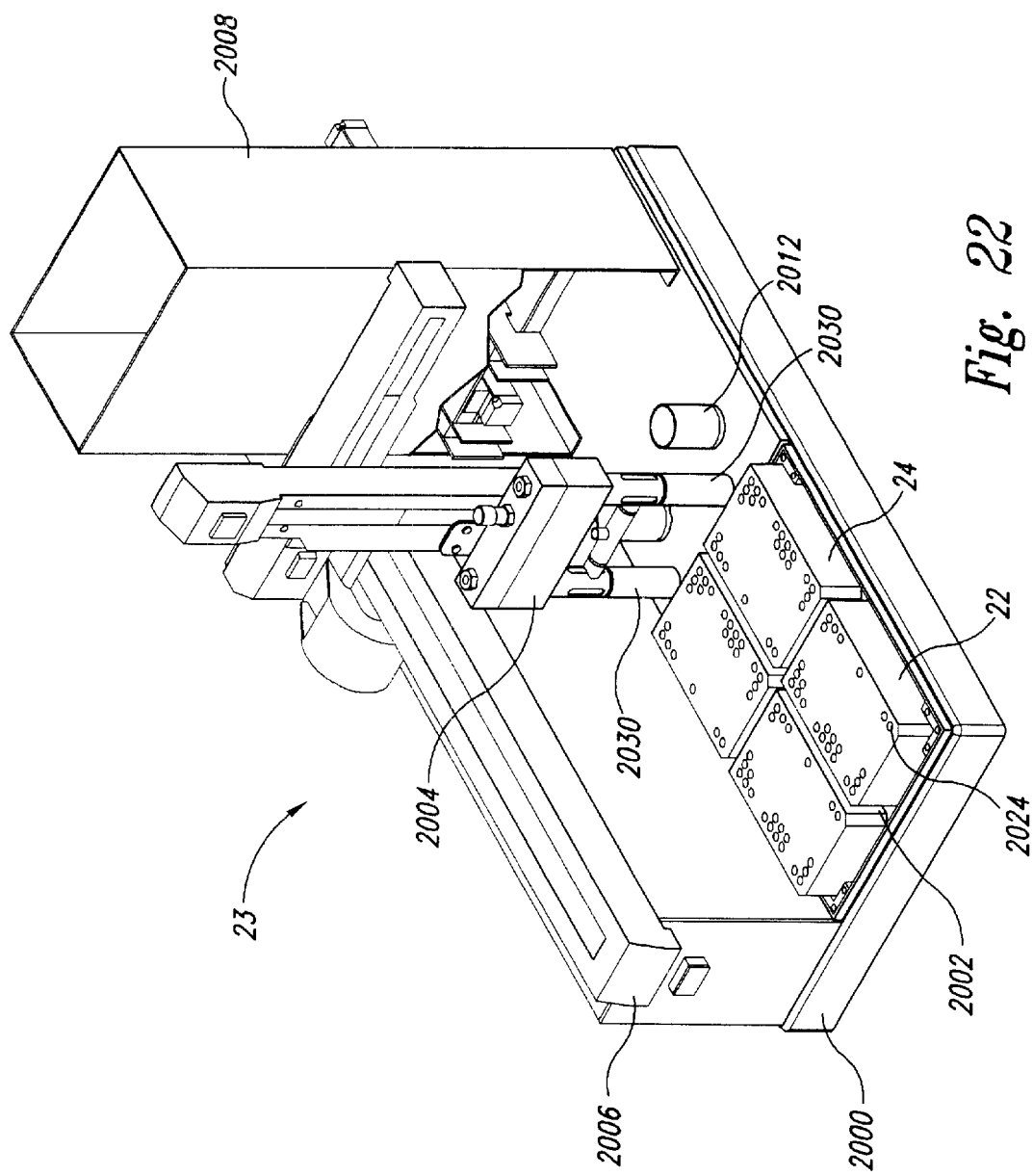

SAMPLE SEPARATION APPARATUS AND METHOD FOR MULTIPLE CHANNEL HIGH THROUGHPUT PURIFICATION

CROSS REFERENCE TO RELATED APPLICATION

This application is a continuation-in-part application to U.S. patent application Ser. No. 09/430,194 entitled "Apparatus and Method for Multiple Channel High Throughput Purification," filed Oct. 29, 1999, now U.S. Pat. No. 6,309,541.

TECHNICAL FIELD

The present invention is directed to apparatus and methods usable for sample purification, and more particularly, to sample separation apparatus and methods usable for high throughput purification of samples.

BACKGROUND OF THE INVENTION

The relationship between structure and functions of molecules is a fundamental issue in the study of biological and other chemistry-based systems. Structure-function relationships are important in understanding, for example, the function of enzymes, cellular communication, cellular control and feedback mechanisms. Certain macromolecules are known to interact and bind to other molecules having a specific 3-dimensional spatial and electronic distribution. Any macromolecule having such specificity can be considered a receptor, whether the macromolecule is an enzyme, a protein, a glycoprotein, anantibody, or an oglionucleotide sequence of DNA, RNA, or the like. The various molecules which bind to receptors are known as ligands.

A common way to generate ligands is to synthesize molecules in a stepwise fashion in a liquid phase or on solid phase resins. Since the introduction of liquid phase and solid phase synthesis methods for peptides, oglionucleotides, and small organic molecules, new methods of employing liquid or solid phase strategies have been developed that are capable of generating thousands, and in some cases even millions of individual compounds using automated or manual techniques. A collection of compounds is generally referred to as a chemical library. In the pharmaceutical industry, chemical libraries of compounds are typically formatted into 96-well microtiter plates. This 96-well formatting has essentially become a standard and it allows for convenient methods for screening these compounds to identify novel ligands for biological receptors.

Recently developed synthesis techniques are capable of generating large chemical libraries in a relatively short period of time as compared to previous synthesis techniques. As an example, automated synthesis techniques for sample generation allows for the generation of up to 4,000 compounds per week. The samples, which contain the compounds, however, typically include 20%–60% impurities in addition to the desired compound. When sample impurities are screened against selected targets, such as a novel ligand or biological receptors, the impurities can produce erroneous screening results. As a result, samples that receive a positive result from initial screening must be further analyzed and screened to verify the accuracy of the initial screening result. This is verification process requires that additional samples be available. The verification process also increases the cost and time required to accurately verify that the targeted compound has been located.

Samples can be purified in an effort to achieve an 85% purity or better. Screening of the purified samples provides more accurate and meaningful biological results. Conventional purification techniques, however, are very slow and expensive. As an example, conventional purification techniques using high-pressure liquid chromatography (HPLC) take approximately 30 minutes to purify each sample. Therefore, purification of the 4,000 samples generated in one week would take at least 2000 hours (i.e. 83.3 days or 2.77 months).

Conventional purification techniques, such as HPLC, also require large volumes of solvents and result in large volumes of waste solvent. Disposal of the solvents, particularly halogenated solvents, must be carefully controlled for legal and environmental reasons, so the disposal process can be laborious and very costly. Disposal of non-halogenated solvents is less rigorous. Accordingly, when halogenated and non-halogenated solvents are used, the waste solvents are separated. The separation process of large volumes of solvents, however, can be a difficult process to perform efficiently and inexpensively. Accordingly, purification of large chemical libraries can be economically prohibitive. Therefore, there is a need for a faster and more economical manner of purifying samples of large chemical libraries, Supercritical fluid chromatography (SFC) provides faster purification techniques than HPLC. SFC utilizes a multiphase flow stream that includes a gas, such as carbon dioxide, in a supercritical state, a carrier solvent and a selected sample. The flow stream passes through a chromatography column, and is then analyzed in an effort to locate target compounds. SFC is beneficial because the solvent and sample are carried by the gas and the amount of solvent needed during a purification run is substantially less than the volume used in HPLC. Also, the amount of waste solvent at the end of a run is substantially less, so less waste solvent needs to be handled. SFC, however, requires pressure and temperature regulation that is difficult to control accurately and reliably long term.

There are many different configurations of the purification instruments. They typically share commonality in the concept wherein that samples are delivered to a chromatography instrument where compounds are separated in time, and a fraction collector collects the target compound. In order for these instruments to maintain the high throughput process, the instruments must be able to handle large sample numbers, as well as large samples in terms of mass weight and solvent volume. Tradition would specify the use of a semiprep or prep scale chromatography system for a typical milligram synthesis. While this is achievable, it has a low feasibility in a high throughput environment because several issues become apparent in such practice: large solvent usage, generation of large amounts of solvent waste, expensive large-bore columns, and relatively large collection volumes of target compounds. If the proper flow rate or column size is not used, sufficient chromatographic purity will not be achieved.

A variety of column configurations have been developed in an effort to improve the chromatographic results. U.S. Pat. No. 4,554,071 discloses a pre-column for high pressure pre-concentration of material to be chromatographed when the substances are provided in trace amounts. The pre-column is a vessel-shaped body that narrows internally at both ends and that is packed with a selected carrier material. The pre-column is connectable to a conventional chromatography column. Liquid sample is added at high pressure into the narrowed top end, and the selected components are absorbed by the carrier material. The non-absorbed fluid is drained from the pre-column through a separate outlet tube not connected to the chromatography column. The concentrated material is eluted with a solvent or solvent mixture and the concentrated sample and solvent are then loaded into the chromatographic column. This concentration process and subsequent separation process through the column can utilize a large amount of solvent to achieve a desired separation of lo the sample.

U.S. Pat. No. 4,719,011 discloses a modular, high pressure liquid chromatography column. The column includes segments with flanged sections that can be combined to increase or decrease the column length. Segments having different inner diameters can also be combined to provide an inner diameter deemed necessary to provide the type of chromatography for the mobile phase being treated. Accordingly, the same modular components are usable in different combinations for different chromatographic runs. The mass sample and solvent volume, however, dictate the diameter and length of the column to be constructed with these modular segments.

Columns used for high throughput processes must be able to handle large sample numbers and large samples in terms of mass weight and solvent volume. Conventional chromatography for large samples typically uses large-bore columns and large volumes of solvent. If the proper flow rate or column size is not used, the desired chromatographic purity will not be achieved. As a result, chromatography of large samples results in large solvent usage, generation of large amounts of solvent waste, increased expense of replacing large-bore columns, and relatively large collection volumes of target compounds. Accordingly, there is a need for a chromatographic column for high throughput purification systems that overcomes drawbacks experienced by the prior art.

Further drawbacks experienced with high throughput purification techniques include durability of components to accommodate the high pressures, high volumes, or high flow rates of samples through the purification system. The purification system requires extreme accuracy and very high tolerances to avoid cross-contamination and to ensure purified compounds. The system components, thus, must be sufficiently durable to accept the aggressive environment while still providing the accurate results required. If the components are not sufficiently durable and they break or require repair too quickly, the purification system must be taken out of service to replace or repair the components.

A further drawback experienced in conventional purification processes of large chemical libraries includes sample management during the purification process. As an example, the chemical libraries are typically maintained in sets of 96-well microtiter plates, wherein each well includes a separate sample. Each sample is carefully tracked by its "well address" within the microliter plate. When a sample or portion of a sample is removed for purification from a selected well of a microtiter plate, the purified sample is typically collected in a separate container, processed, and eventually returned to a receiving well in a similar microtiter plate. That receiving well preferably has a corresponding well address in the microtiter plate so as to maintain the accuracy of the library records regarding sample location in the respective microtiter plate.

Conventional purification processes typically require the reformatting of a purified sample because the large collected volumes of fluid (e.g. the solvent that contains the purified sample) is greater than the volume of a receiving well in a conventional microtiter plate. The large collected volumes must be reduced to a volume that fits into the microtiter plate's well. The reduced volume of fluid containing the purified sample is also tracked and deposited into the appropriate well of the receiving microtiter plate that correctly maps to the well location from which the sample was taken at the start of the purification run. Such reformatting of purified samples into the receiving microtiter plate increases the time requirements and cost of the purification processes. Therefore, there is a need for a purification process that allows for quick and economical purification of samples that result in purified samples being collected directly to microtiter plates mapped directly to the original plate.

SUMMARY OF THE INVENTION

The present invention is directed to chromatographic column apparatus and methods usable for multiple channel high throughput purification of samples from a chemical library that overcome drawbacks experienced in the prior art. In an illustrated embodiment of utilizing a chromatographic column in accordance with the present invention, the process of multiple channel high throughput purification simultaneously purifies a plurality of samples, such as four samples, from a chemical library.

The process includes simultaneously purifying by supercritical fluid chromatography (SFC) all four samples in four channels of a purification system. The method includes passing a first sample along a SFC flow path of the first channel, separating the first sample into sample portions by passing the sample through a chromatographic column in accordance with one embodiment of the invention, and spacing the sample portions apart from each other along at least a portion of the first fluid path.

One embodiment of the invention provides a high throughput liquid chromatography column assembly configured to receive a selected injection of a sample for flow therethrough at a selected flow rate to achieve chromatographic separation of the sample. The sample has a selected mass weight and fluid volume. The assembly includes a loading column with a loading chamber therein having a first inner diameter and a first length. The loading chamber is sized to retain a selected volume of a solid phase packing material onto which the sample is loaded and spatially distributed within the loading chamber. The volume of the loading chamber is sufficient to fully load the sample therein, but the length of the loading chamber is insufficient to achieve the selected chromatographic separation of the sample as the sample passes through the packing material.

A separation column with a separation chamber is positioned to receive the sample from the loading column. The separation chamber has a diameter smaller than the loading column's diameter, and a length greater than the loading column's length. The separation chamber retains a solid phase packing material therein, and the separation chamber's length is sufficient to achieve the selected chromatographic separation as the sample passes through the packing material at the selected flow rate. The separation column's inner diameter is such that the separation chamber has a volume over the same length as the loading column's length that is insufficient to act as a loading area for the entire selected sample.

The pressure of the supercritical fluid in the flow stream is regulated with a backpressure regulator and a pressure relief valve. The method also includes moving the separated sample portions along the fluid path, and detecting at least one sample portion flowing along the fluid path. The method further includes diverting a sampling away from the sample portion, directing the sampling to an analyzer while the remainder of the sample portion continues along the fluid path. The sample is analyzed with the analyzer, which determines if the one sample portion has selected sample characteristics. The method also includes collecting the one sample portion in a first receptacle, such as a well of a first microtiter plate, only if the sample portion has the selected sample characteristics. If the sample portion does not have the selected sample characteristics, the sample portion is collected in a second receptacle, such as a corresponding well in a second microtiter plate.

The multiple channel high throughput purification method of this illustrated embodiment further includes purifying a second sample along a second channel substantially simultaneously with the purification of the first sample. Purifying the second sample includes passing the second sample along a second flow path of the second channel, separating the second sample into sample portions, and spacing the sample portions apart from each other along at least a portion of the second fluid path. The method also includes moving the separated sample portions along the second fluid path, and detecting at least one of the sample portions flowing along the second fluid path. The method includes regulating the second sample's pressure along the flow path. The method further includes taking a sampling from the one sample portion and directing the sampling to the same analyzer used for the first channel. The remainder of the sample portion continues to flow along the second fluid path.

The method also includes analyzing the second sampling with the analyzer, wherein the first and second samplings are analyzed separately in accordance with a selected analysis priority protocol. The analysis of the second sampling determines if the sample portion has selected sample characteristics. The method further includes collecting the sample portion in a separate receptacle, such as a separate well in the first microtiter plate identified above, only if the sample portion has the second selected sample characteristics. If the sample portion does not have the selected sample characteristics, the sample portion is collected in another receptacle, such as a separate well in the second microtiter plate identified above.

In one embodiment, the method of high throughput purification includes purifying third and fourth samples along corresponding third and fourth channels in a manner similar to the purification discussed above regarding the first and second samples. In this embodiment, the same analyzer is used to analyze samplings from all four samples. The samplings are all analyzed separately and in accordance with the selected analysis priority protocol.

The process is also directed to a multiple channel high throughput purification system for substantially simultaneously purifying a plurality of samples from a chemical library. In one illustrated embodiment, the system includes a controller and a sample analyzer coupled to the controller, wherein the analyzer is configured to determine whether the samplings have selected sample characteristics. First, second, third, and fourth purification channels are coupled to the sample analyzer. The first purification channel includes a separation device positioned to receive a sample flow and to separate a first sample into sample portions so the sample portions are spaced apart from each other in the sample flow. A detector is positioned to receive the sample flow from the separation device and to detect at least one sample portion within the first sample. An adjustable backpressure regulator receives the flow stream from the detector and controls the pressure of the flow stream within the first channel.

A microsampling device is positioned to receive the sample flow from the backpressure regulator and is movable between open and closed positions while allowing a substantially continuous flow stream to pass through the device. In the closed position, the microsampling device blocks the flow stream from passing to the analyzer and allows the flow stream continues to flow through the device. In the closed position, the microsampling device also allows a substantially continuous flow of carrier fluid to pass therethrough to the analyzer. In the open position, the microsampling device directs a sampling of at least the one sample portion to the analyzer for analysis, while a remainder of the one sample portion in the sample flow moves substantially uninterrupted through the microsampling device.

A pressure relief valve receives the remainder sample flow from the microsampling device and maintains a selected pressure in the sample flow downstream of the microsampling device. A flow directing valve is in fluid communication with the first flow path and is positioned to receive the sample flow downstream of the pressure relief valves. The flow directing valve is moveable to a first position to direct the one sample portion in one direction if the analyzer has determined that the one sample portion has the selected sample characteristics. The flow directing valve is movable to a second position to direct the one sample portion in another direction if the analyzer has determined that the one sample portion does not have the selected sample characteristics. A first receptacle, such as a well of a microtiter plate, is positioned to receive the one sample portion from the flow directing device when the flow directing device is in the first position because the sample portion has the selected characteristics. A second receptacle, such as a well in a second microtiter plate, is positioned to receive the one sample portion when the flow directing device is in the second position because the sample portion does not have the selected characteristics, The second purification channel of the purification system includes a separation device positioned to receive a second sample flow and to separate a second sample into sample portions. A separate detector is coupled to the separation device and is positioned to receive the second sample from the separation device. The detector is configured to detect at least one of the sample portions within the sample flow. A microsampling device is positioned to receive the sample flow from the detector and is movable between open and closed positions. When the microsampling device is in the closed position, the microsampling device allows the second sample flow to pass therethrough while and blocks the flow from passing to the analyzer. In the open position, the microsampling device directs a sampling of the one sample portion to the analyzer for analysis, while the remainder of the sample portion continues along the second flow path substantially uninterrupted.

A back pressure regulator and a pressure relief valve receive the second sample flow upstream and downstream, respectively, of the microsampling device to selectively control the pressure of the second sample flow along the second purification channel. A flow directing valve is in fluid communication with the second flow path and is positioned to receive the sample flow therethrough. The flow directing valve is moveable to a first position to direct the one sample portion in one direction if the analyzer has determined the sample portion has the selected sample characteristic. The flow directing valve is moveable to a second position to direct the one sample portion in another direction if the analyzer has determined that the sample portion does not have the selected sample characteristics. A waste receptacle receives the remainder of the flow that does not include the sample portion.

A receptacle, such as a separate well in the first microtiter plate, is positioned to receive the sample portion from the flow directing device when the flow directing device is in the first position because the sample portion has the selected characteristics. Another receptacle, such as a separate well in the second microtiter plate, is positioned to receive the sample portion when the flow directing device is in the second position because the sample portion does not have the selected characteristics.

In one embodiment, the purification system includes third and fourth purification channels that purify third and fourth samples substantially simultaneous with the purification of the first and second samples. Each of the third and fourth purification channels are coupled to the same analyzer and direct the sample portions to receptacles, such as wells in the first and second microtiter plates, discussed above.

An aspect of the system provides a microsample or flow splitter valve for use in the high throughput purification system for purifying a selected sample from a chemical library. The purification system has a sample flow path, a carrier fluid flow path, and a sample analyzer in fluid communication with the sample and carrier flow paths. The microsample valve includes a valve body having an interior chamber therein, and sample flow inlet and outlet ports in fluid communication with the sample flow path and with the interior chamber. The valve body has a carrier fluid flow port in fluid communication with the carrier fluid flow path, and an outflow port channel in fluid communication with the analyzer. A stem is slidably disposed in the interior chamber and is moveable between first and second positions within the chamber. The stem has a fluid bypass channel that communicates with the sample inlet port and the outflow port when in the first position to allow a selected portion of the sample to flow to the analyzer. The stem blocks the carrier flow port when in the first position to prevent fluid from the carrier fluid flow path from moving into the outflow port.

The fluid bypass channel in the stem communicates with the carrier flow port and with the outflow port when in the second position to allow selected carrier fluid to flow through the valve body to the analyzer. The stem blocks the sample flow inlet port from communicating with the outflow port when in the second position to prevent the sample flow from flowing to the outflow channel.

Another aspect of the system also includes an automated fraction collection assembly that retains the microtiter plates in a fixed position and dispenses the sample portions into the selected wells in the microtiter plates. The fraction collection assembly includes a dispensing needle through which the sample portion is dispensed into disposable expansion chambers and then into the microtiter plate. The dispensing needle is mounted on a dispensing head adapted to extend into a disposable expansion chamber into which the sample portion is condensed and then dispensed into the microtiter plate.

The dispensing head is movable from a pick-up position, where the expansion chambers are picked up, to a collection position over the microtiter plates, where the sample portions are dispensed into the selected well of the microtiter plate. The dispensing head is also movable from the dispensing position to a chamber drop-off position, where the expansion chambers are released into a waste receptacle, so the dispensing needles are exposed. The dispensing head is further movable to a wash position at a wash station on the fraction collection assembly, where the dispensing needles are washed to avoid cross-contamination between samples.

BRIEF DESCRIPTION OF THE DRAWINGS

FIG. 15 is a plan view of a valve body of the microsample valve of

FIG. 22 is an isometric view of the fraction collection assembly of FIG. 19 shown in a rinse position.

DETAILED DESCRIPTION OF THE INVENTION

The structure and function of exemplary embodiments of the present invention can best be understood by reference to the drawings. The same reference numbers may appear in multiple figures. The reference numbers refer to the same or corresponding structure in those figures.

Figure 1:
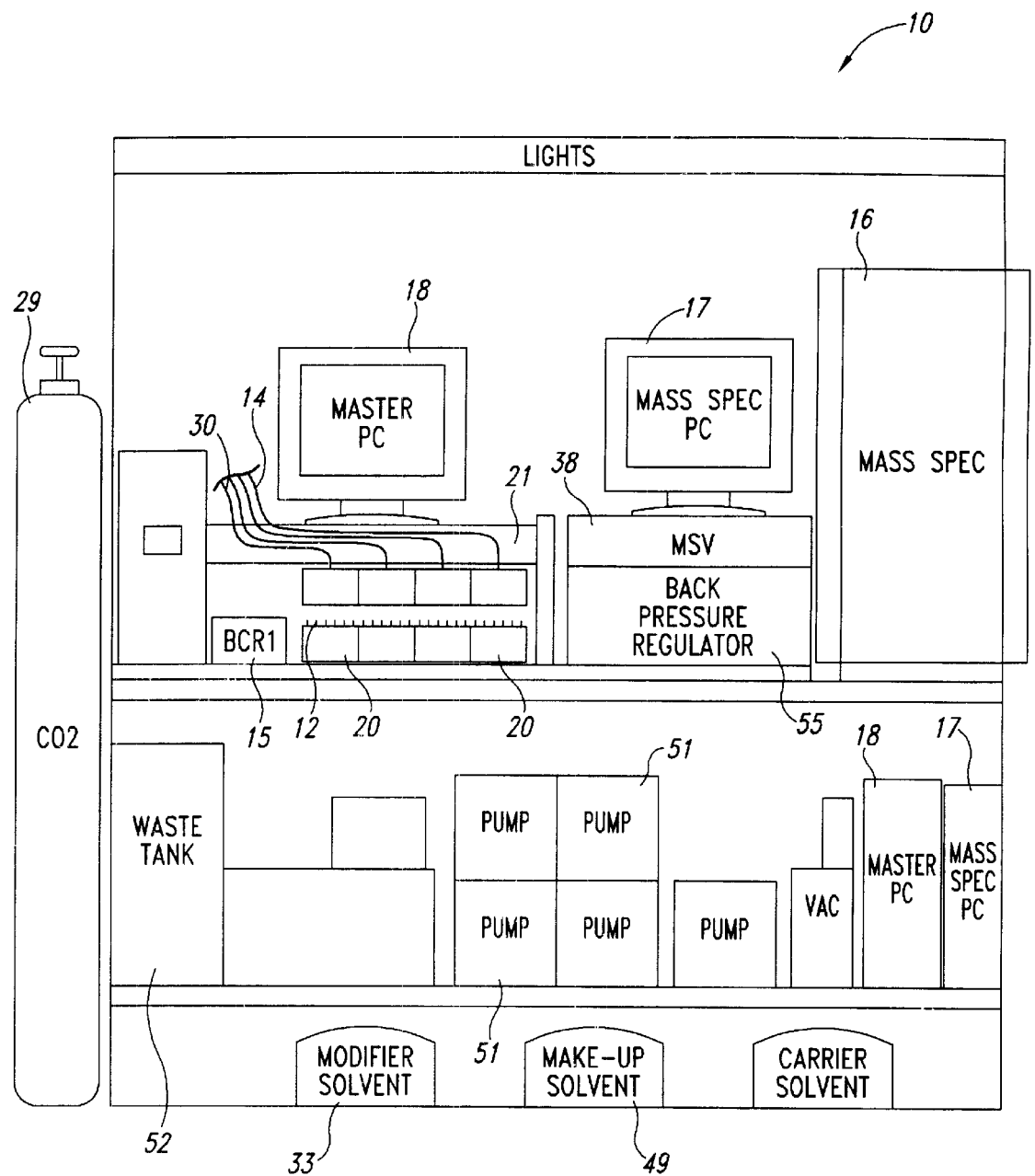
FIG. 1 is a schematic view of one portion of a multiple channel high throughput purification system with a chromatographic column in accordance with an embodiment of the present invention.
Figure 2:
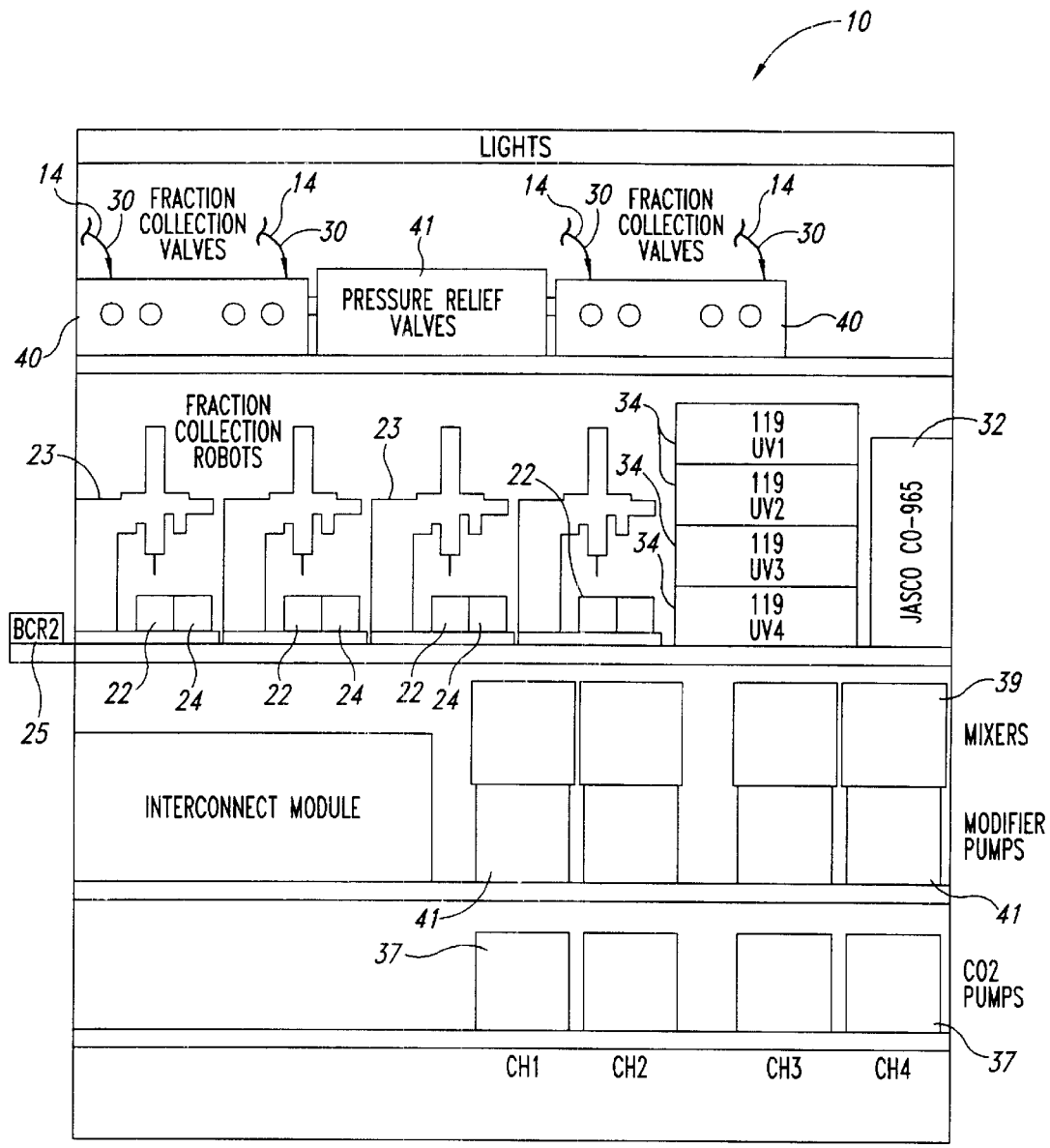
FIG. 2 is a schematic view of another portion of the multiple channel high throughput purification system of FIG. 1.
Figure 3A:
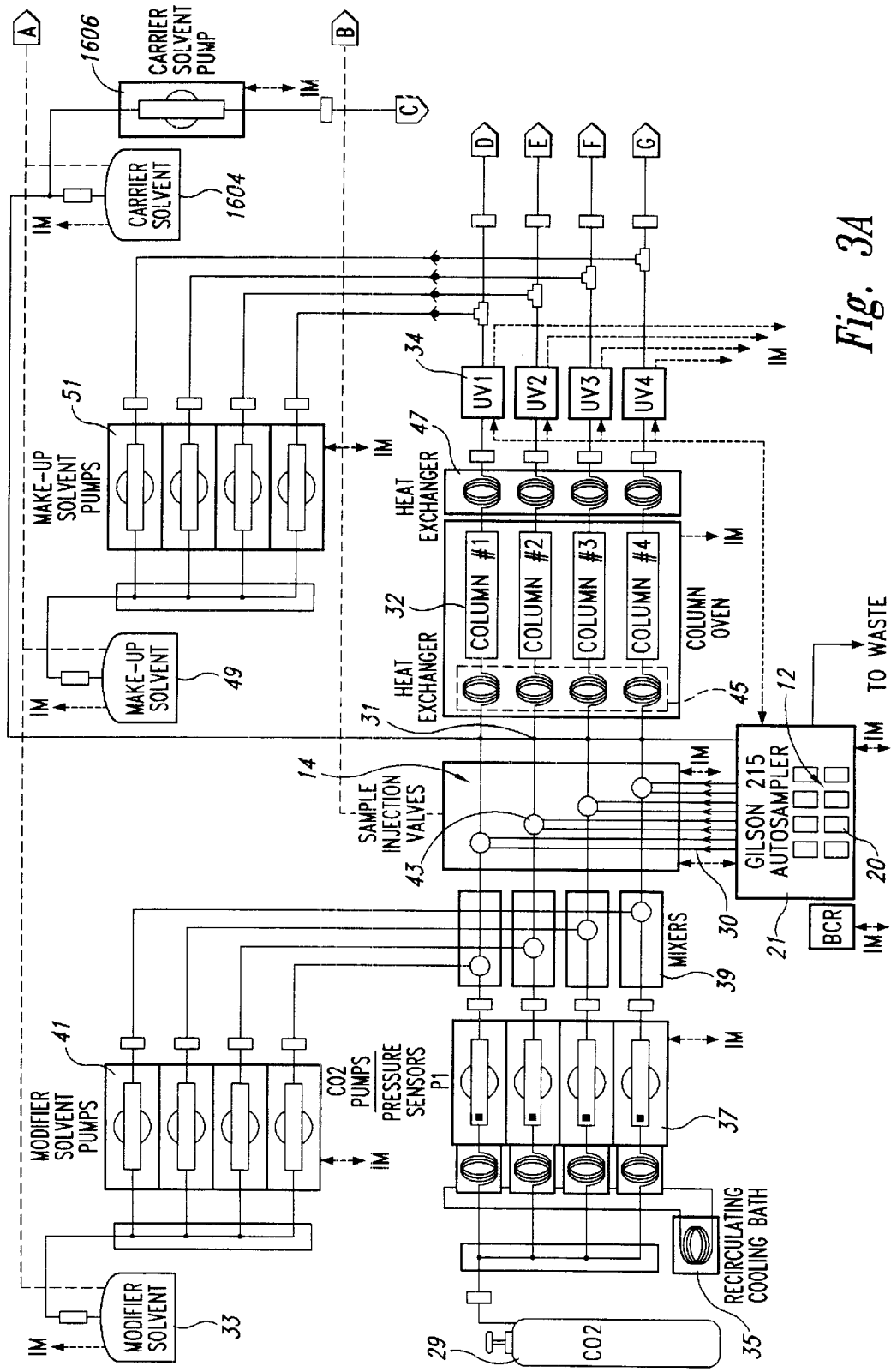
FIGS. 3A and 3B are schematic veiw of the multiple channel high throughput purification system of FIGS. 1 and 2, wherein the system has four channels.
Figure 3B:
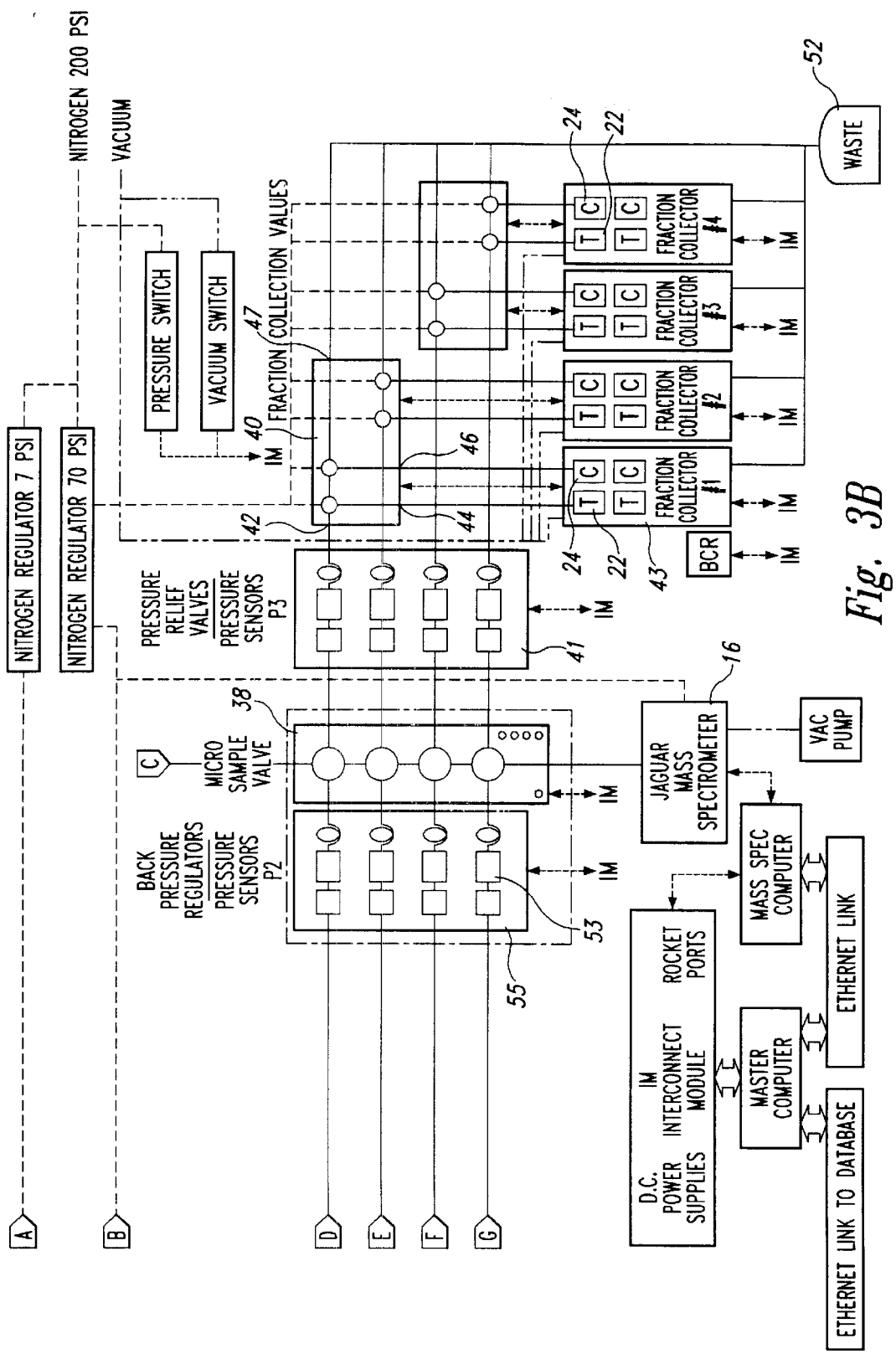

A multiple channel high throughput purification system 10 having a chromatography column 32 in accordance with an illustrated embodiment is shown in FIGS. 1–3, and components of the system are shown in FIGS. 4–22. The illustrated purification system 10 is configured to simultaneously purify four samples 12 from a chemical library, wherein each sample is purified along a respective purification channel 14 in the system. Purification in the illustrated embodiment is achieved by chromatography, and more particularly by super critical fluid chromatography (SFC), discussed in greater detail below.

Each channel 14 receives a selected sample from a supplying microtiter plate 20. Each channel 14 is coupled to a common analyzer, such as a mass spectrometer 16 that analyzes selected portions of the samples in accordance with a predetermined analysis priority protocol. In one embodiment, the analyzer includes a plurality of compound identification devices. In the illustrated embodiment, each supplying microtiter plate 20 includes a bar code or other selected symbology or tracking mechanism that provides information specific to that supplying microtiter plate. The purification system 10 includes a bar code reader 15 or the like that identifies the specific supplying microtiter plates 20 used for each purification run.

The components of each channel 14, including the mass spectrometer 16 and the bar code reader 15, are coupled to a computer controller that monitors and controls operation of the components during a purification run. The mass spectrometer 16 is also connected to a computer 17 that can provide a user with additional control or monitoring capabilities during a purification run.

After each sample 12 is analyzed by the mass spectrometer 16, a substantially purified sample portion is distributed directly into a corresponding well of a receiving microtiter plate 22 (FIG. 2) or another selected sample collector. The other portions of the sample detected by the detector, known as reaction by-products, sometimes referred to as crudes, are distributed directly into a corresponding well in a second microtiter plate 24, also illustrated in FIG. 2. Accordingly, the four samples 12 are drawn from the supplying microfiter plate purified, and each sample is deposited directly into a corresponding well location in two receiving microtiter plates 22 and 24, one containing the purified target compound and the other containing the reaction by-products. In one embodiment, the four samples are drawn from the supplying microtiter plate sequentially by the same drawing needle assembly. In an alternate embodiment, the four samples are drawn substantially simultaneously by a drawing assembly having four drawing needles.

The receiving microtiter plates 22 and 24 have bar codes or the like on them, and a bar code reader 25 (FIG. 2) is provided adjacent to the receiving microtiter plates. The second bar code reader 25 is also coupled to the computer controller 18 (FIG. 1) to identify and track the samples deposited into the selected wells of each microtiter plate. The purified target compounds in the microtiter plates 22 and 24 can then be screened in a selected manner in an effort to locate a specific target compound.

The microtiter plates 22 are securely retained in an automated fraction collection assembly 23 coupled to the computer controller 18 (FIG. 1).

The fraction collection assembly 23 directs selected sample portions of either purified target components or purified reaction by-products to selected wells of the microtiter plates 22 or 24. The fraction collection assembly 23 is automated and configured to pick up, clean, disposable or reusable expansion chambers in which vaporous sample portions are condensed and then delivered to the microtiter plates 22 or 24. The fraction collection assembly 23 includes a wash station in which sample dispensing needles are washed after a sample portion is delivered to the respective microtiter plate and before the next set of clean expansion chambers are picked up for delivery of the next sample portions.

In the purification process of the illustrated embodiment, selected supplying microtiter plates 20 are identified by the bar code reader 15 and positioned on an autosampler 21 (FIG. 1). In one embodiment, the autosampler 21 is a Gilson 215 autosampler, manufactured by Gilson, Inc. of Middleton, Wis. As best seen in the schematic diagram of FIG. 3, each sample is drawn by the autosampler 21 from a selected well of a supplying microtiter plate 20 and is fed into a sample flow path 30 of a respective one of the four channels 14. The four samples 12 are substantially simultaneously introduced into the respective purification channels 14. Although the illustrated embodiment substantially simultaneously purifies four samples 12, other numbers of samples can be simultaneously purified with a system in accordance with the present invention.

As best seen in FIG. 3, the sample 12 is combined with carbon dioxide from a $CO_2$ source 29 and a modifier solvent from a solvent source 33 to form a carrier flow that flows through the respective channel 14 at a selected flow rate. The carbon dioxide flows through a heat exchanger 36 is chilled with a recalculating cooling bath 35 and is pumped via a $CO_2$ pump 37 to a mixer 39. The flow of $CO_2$ is also passed through a pulse damper to minimize any pulsation caused by the pump 37. The modifier solvent flows through a solvent pump 41 into the mixer 39 where the solvent is mixed with the carbon dioxide. The carbon dioxide and solvent mixture then flows to a sample injection valve 43, where the sample 12 is received from the autosampler 21 is combined with the carrier flow to form the sample flow 31.

The sample flow 31 is passed through a heat exchanger 45 at which time the fluid becomes supercritical, and then a separation media, such as an SFC column 32, that separates the sample components within the sample flow 31. Accordingly, each sample component is spaced apart from the other components as the sample flow exits the SFC column 32 and moves through the purification channel 14.

Figure 4:
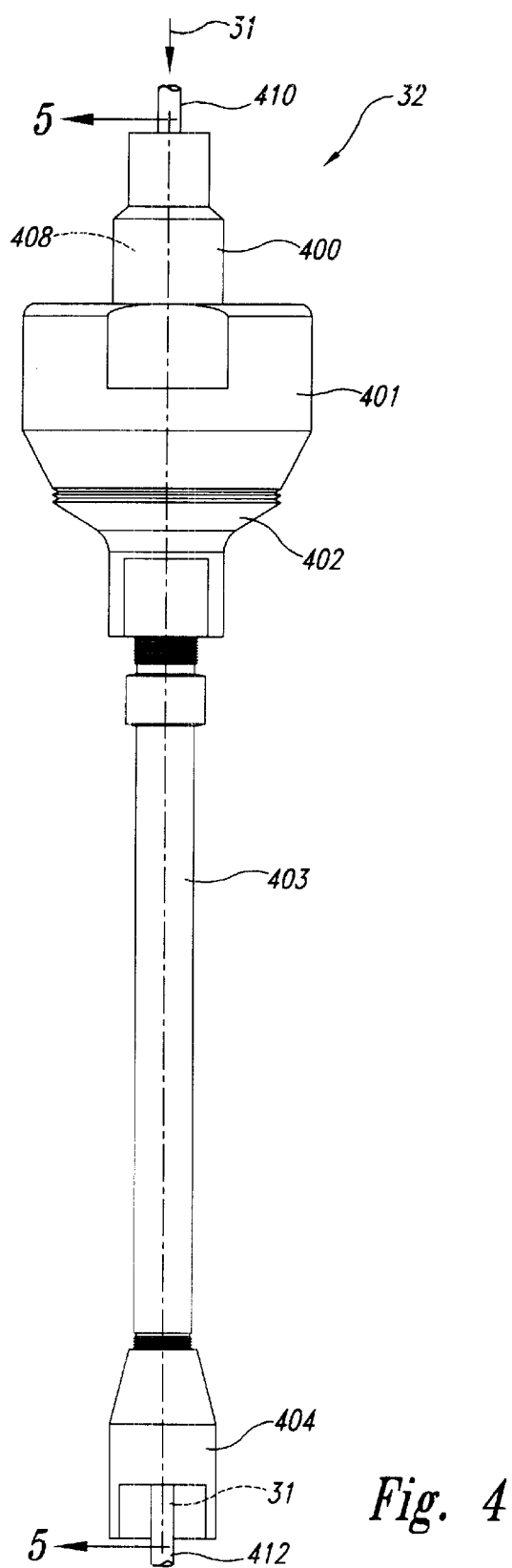
FIG. 4 shows a side elevation view of a two-piece chromatography column of the purification system of FIG. 3 in accordance with one embodiment of the invention.
Figure 5:
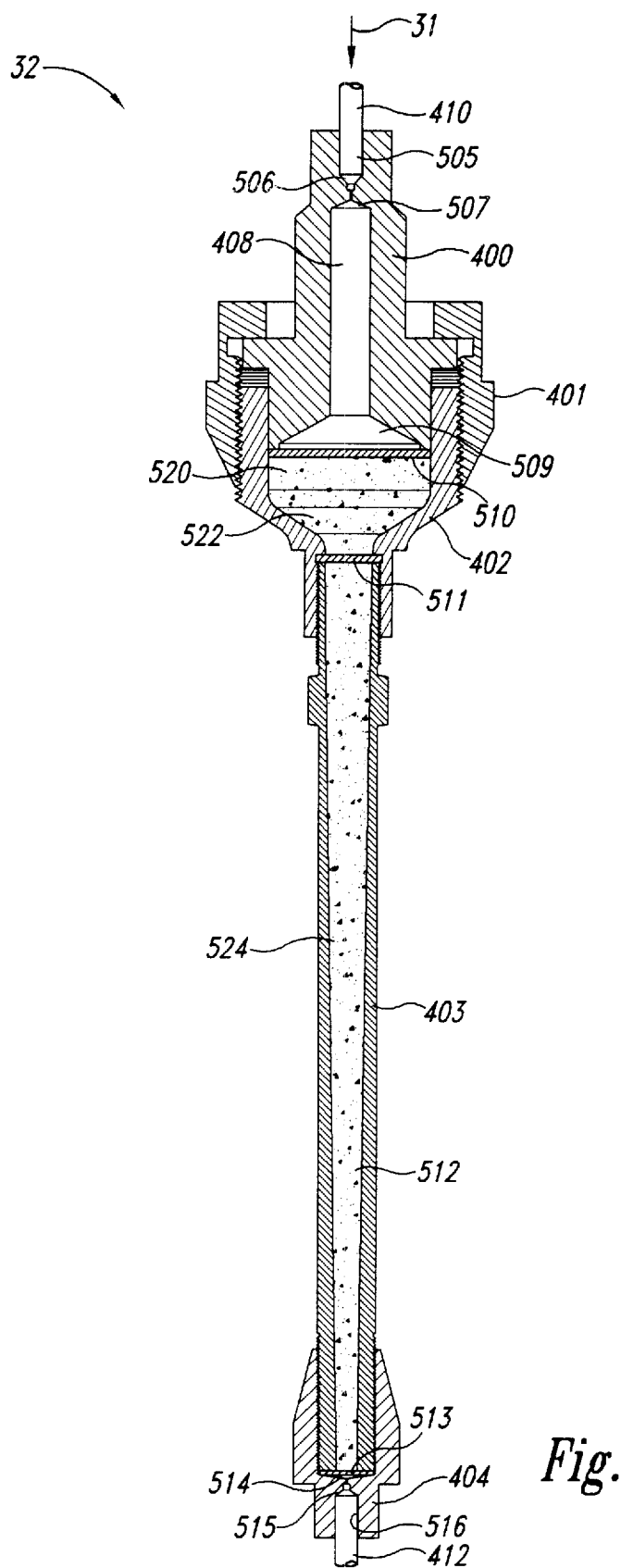
FIG. 5 shows a cross-sectional view of the two-piece column taken substantially along line 5—5 of FIG. 4.

In one embodiment of the invention, the column 32 is a two-piece column, as illustrated in FIGS. 4 and 5, for use in supercritical fluid chromatography. As best seen in FIG. 4, the components of the column 32 include an upper dilution body 400 that defines that a dilution chamber 408 therein.

The top portion of the dilution body 400 is connected to an inlet tube 410 through which the sample flow 31 passes and moves into the column 32. The upper dilution body 400 is connected to a loading body 402 and securely retained in place by a top end cap 401. The dilution chamber body 400 is compressed downwardly by the top end cap 401 that screws externally onto the threads of the loading body 402. fn an alternate embodiment for use in liquid chromatography, the dilution chamber is not needed, so the column 32 does not include the dilution body attached to the loading body.

The dilution chamber body 400, the top end cap 401, and the loading body 402 of the illustrated embodiment are made from an inert material, such as stainless steel. In alternate embodiments, other inert materials can be used for construction of the column's components. A separation body 403 at its upper end is attached to the lower portion of the loading body 402. The lower end of the separation body 403 is securely connected to a bottom end cap 404 that connects to an outlet tube 412, through which the separated sample flow 31 exits the column 32.

As best seen in a cross-sectional view of FIG. 5, the sample flow 31 enters the column 32 at a top-threaded port 505 to which an inlet tube 410 is sealed by an external ferrule that seats onto the top ferrule sealing point 506 in the threaded port. The sample flow is directed radially from the inlet tube 410 into the upper dilution chamber 408 by means of an inverted top funnel portion 507. The top funnel portion 507 is substantially conical in geometry and it defines the top of the dilution chamber 408. The main body of the dilution chamber 408 is substantially cylindrical, although it can be constructed with other geometric shapes in alternate embodiments. The bottom of the dilution chamber 408 has an inverted bottom funnel portion 509 that flares radially outwardly from the dilution chamber's main body. Accordingly, the bottom funnel portion 509 flares to a lower opening having a greater diameter than the dilution chamber's main body. The lower opening of the bottom funnel portion 509 is positioned over a top frit 510 located below the dilution chamber 408.

The dilution chamber's entire volume is void of stationary phase material. Dilution of the sample in the sample flow takes place in the dilution chamber 408 as the sample flow moves downwardly through the main body to the bottom funnel portion 509, where the sample flow passes through the top frit 510. The top frit 510 distributes the sample over a column bed 512 in a loading region 520 directly below the top frit 510. Sealing of the dilution chamber 408 is achieved at the top frit 510 where the dilution chamber body 400 fits internally into the loading body 402.

The loading body 402 has a loading region 520 below the top frit 510 and a transition region 522 below the loading region. The loading and transition regions 520 and 522 in the loading body 402 are filled with a stationary phase material, such as cyano, that defines a column bed 512 in the column 32. In alternate embodiments, other stationary phase materials can be used to form the column bed 512. The loading region 520 has an inner diameter approximately two or more times greater than the inner diameter of the separation region 524, and a length of approximately one-half or less than the length of the separation region. In the loading region 520, the sample flow traverses downwardly through the column bed 512 into the transition region 522, which has a conical shape as defined by the loading body 402. The transition region 522 directs the sample flow into the separation region 524 of the column bed 512.

The loading region 520 is wide but short, so the sample is distributed over the wider area of the column bed 512. Accordingly, the sample is spatially distributed across a larger horizontal plane, thus separating it from the non-compatible loading solvent. The column bed 512 has selected absorptive characteristics. The length of the loading region 520 and the depth of the column bed 512 provides a minimum vertical absorptive profile that allows sufficient absorption of the sample onto the stationary phase material forming the column bed. The loading region's length, however, is insufficient for the selected chromatographic separation of the sample for its given mass load and the solvent volume.

Because the loading chamber or region 520 is for loading of the sample rather than for chromatographic separation, the loading chamber does not control the required flow rate for such separation. Instead, the flow rate is determined by the diameter of the separation region 524. Once the sample has been properly loaded into the loading chamber 520, the elution gradient process of the flow will elute the sample and pass it directly to the separation column. The separation region 524 has a smaller diameter than the loading region's diameter, and this smaller diameter controls the flow rate for the sample for its given sample mass and volume. This smaller diameter allows the sample flow to be run at a lower rate, thereby lowering solvent consumption and solvent waste generation.

The top of the separation body 403 is threadably attached to the bottom of the loading body 402 by a threaded connection and is sealed by an adjoining frit 511 sandwiched therebetween. The separation body 403 of the illustrated embodiment is made of stainless steel and is shaped so the interior chamber containing the separation region 524 of the column bed 512 has a tapered cylindrical geometry with a wider upper end and a narrower lower end. The interior chamber of separation region 524 of the column bed 512 is filled with the stationary phase material. The sample flow travels downwardly through the column bed 512 in the separation region 524 past a bottom frit 513 and onto a bottom fluid funnel 514 formed in the bottom end cap 404. The bottom of the separation region 524 is sealed by the bottom end cap 404 screwed externally onto the separation body 403. The bottom frit 513 is sandwiched between the bottom end cap 404 and the separation body 403. The bottom fluid funnel. 514 is conical and directs the fluid into a bottom threaded port 516 formed in the bottom end cap 404 to which the outlet tube 412 can be screwed. The outlet tube 412, when screwed into the outlet port 516, is sealed against the bottom end cap 404 at a bottom ferrule sealing point 515 by use of an external ferule.

In an alternate embodiment illustrated in FIG. 6, the column 32 is a "one-piece" column. In view of the similarities between the two embodiments, components that are the same between the two embodiments are identified in the figures by the same reference numbers for purposes of clarity. The one-piece column is substantially the same as the two-piece column discussed above, with the exception that the loading body 602 and the separation body 603 are integrally formed from a single stainless steel unit to define a One-Piece Loading and Separation (OPLAS) body 617. Accordingly, the upper frit 511 used in the two-piece column is not needed and thus omitted.

Figure 6A:
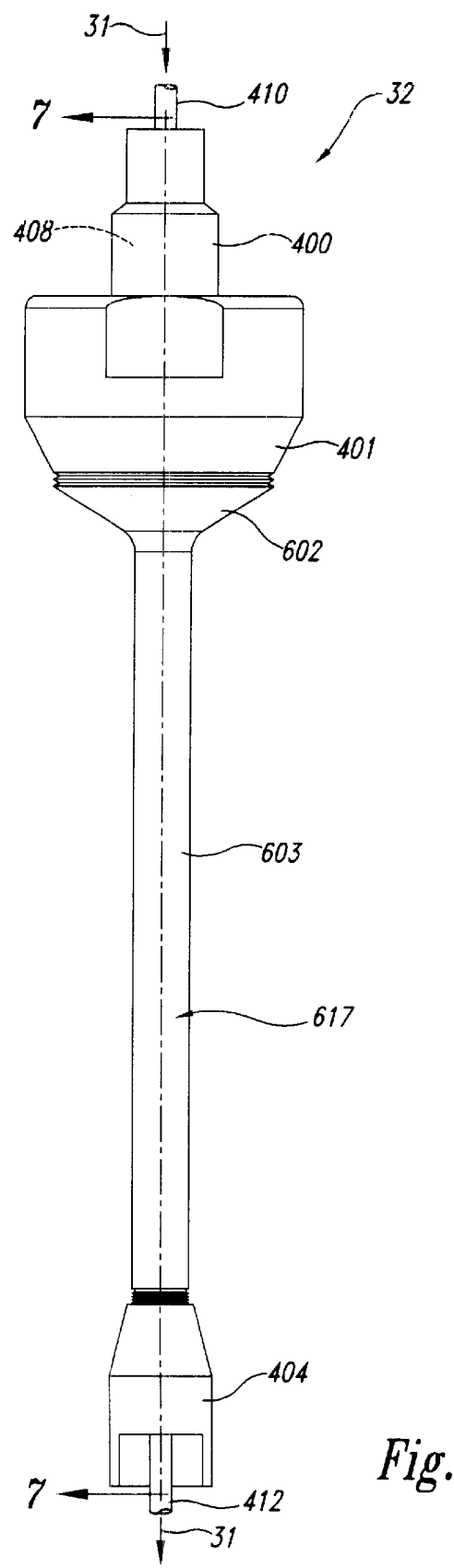
FIG. 6A shows a side elevation view of a one-piece chromatography column in accordance with an alternate embodiment of the invention.
Figure 6B:
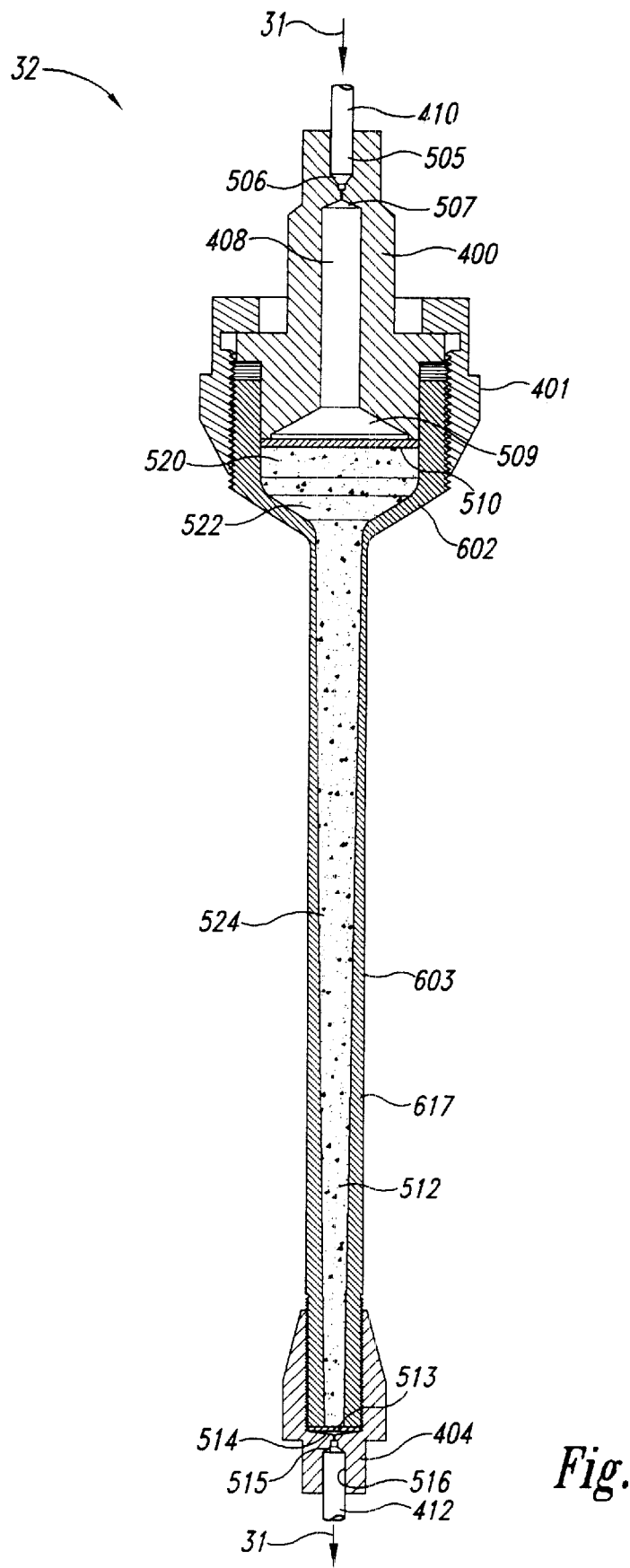
FIG. 6B shows a cross-sectional view of the one-piece column taken substantially along line 6B—6B of FIG. 6A.

As best seen in the cross-sectional view of FIG. 6A, the dilution chamber body 400 fits internally into the OPLAS body 617 and is secured by the top end cap 401 that screws externally onto the OPLAS body. The lower end of the OPLAS body 617 screws internally into the bottom end cap 404. Accordingly, the loading region 520 formed in the OPLAS body 517 has a diameter approximately two or more times greater than the inner diameter of the separation region 524, and a length of approximately one-half or less than the length of the separation region.

Figure 7A:
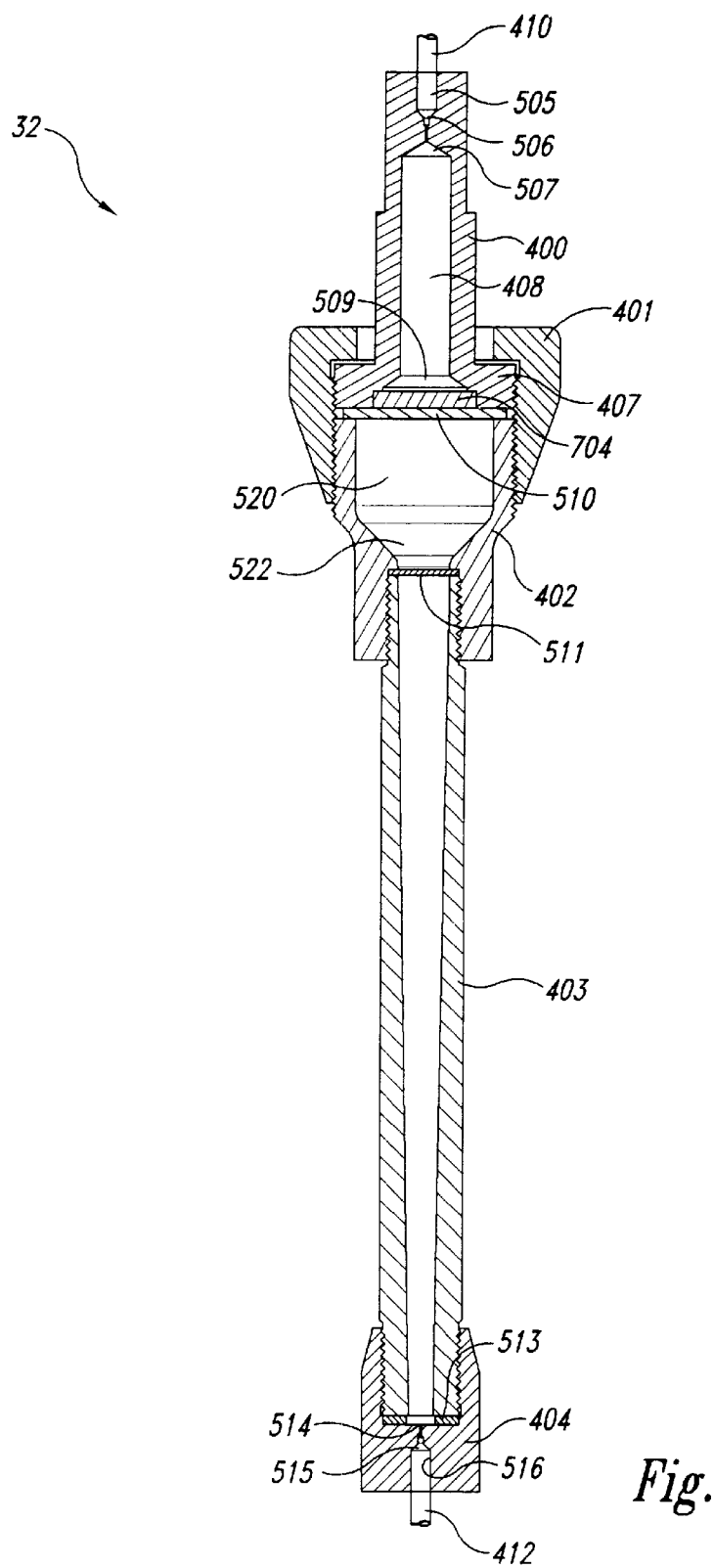
FIG. 7A is a cross-sectional view of a chromatography column in accordance with an alternate embodiment of the invention.

In an alternate embodiment illustrated in FIG. 7A, the column 32 is similar to the "two-piece" column discussed above and shown in FIGS. 4 and 5. The dilution chamber body 400 has a lower end 407 that sits on top of the loading body 402. The dilution chamber body 400 has the same outer diameter as the outer diameter of the loading body 402. The top frit 510 is sandwiched between the lower end 407 of the dilution chamber body 400 and the top of the loading body 402.

In the illustrated embodiment, a support frit 704 is positioned above the top frit 510 and immediately below the bottom funnel portion 509 of the dilution chamber 408. When the dilution chamber 408 is filled with an inert material, such as plastic or stainless steel beads, the support frit 704 retains the inert media within the dilution chamber 408. The support frit 704 also provides support to the top frit 510 to prevent it from bulging.

Figure 7B:
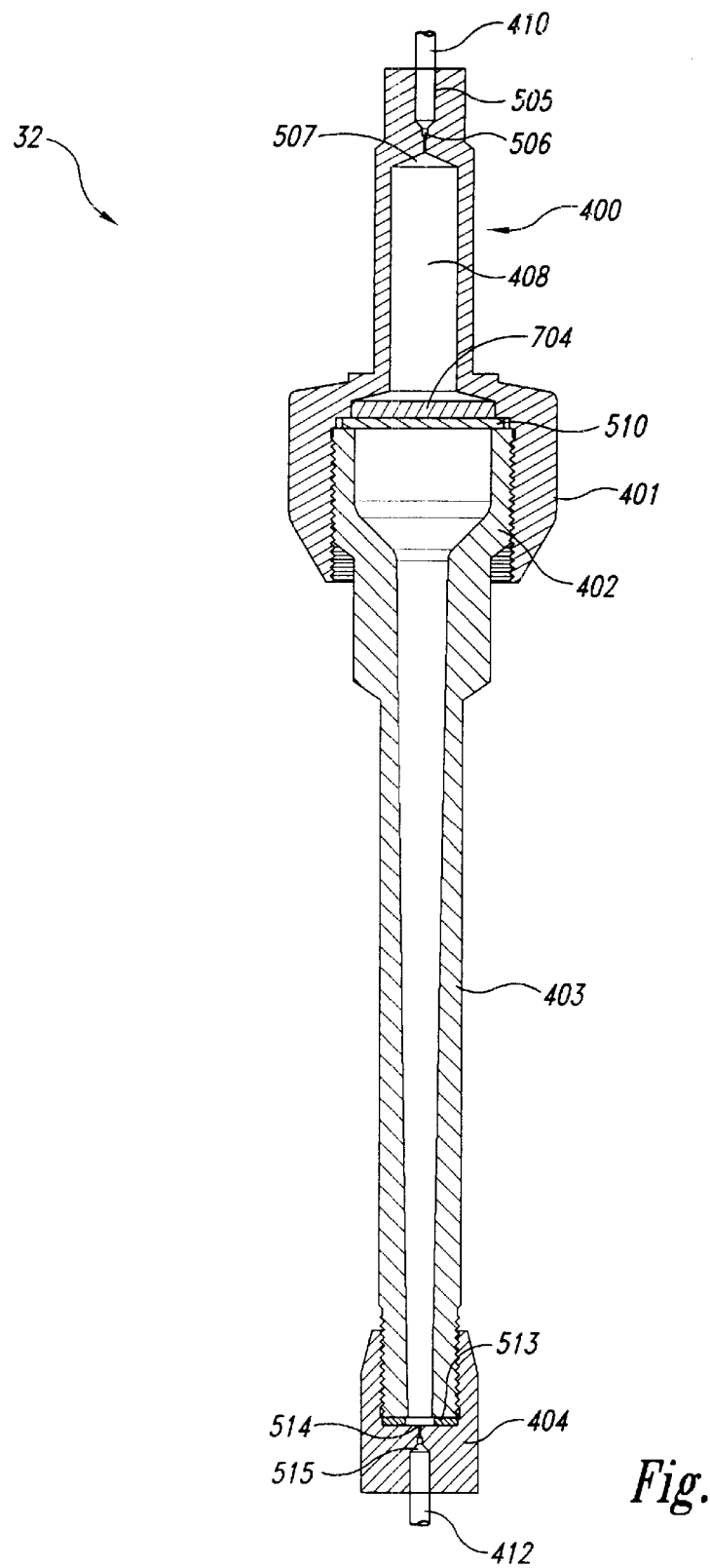
FIG. 7B is a cross-sectional view of another alternate embodiment of a chromatography column according to the invention.

In another alternate embodiment illustrated in FIG. 7B, the column 32 is similar to the "one-piece" column discussed above and shown in FIGS. 6A and 6B. The dilution chamber body 400, however, is integrally connected to the top end cap 401 that threadably engages the loading body 402. The dilution chamber body 400 and top end cap 401 are positioned to sandwich the top frit 510 against the top of the loading body 402. This embodiment also includes the support frit 704, as discussed above, positioned to retain any inert media when used within the dilution chamber 408 and to support the top frit 510 against bulging. The loading body 402 is integrally connected to the separation body 403.

The separation body 403 of the alternate embodiments illustrated in FIGS. 7A and 7B are shown with a generally conical-shaped separation region 524. In alternate embodiments, the separation region 524 can have a cylindrical shape with a constant cross-sectional area along its length.

Figure 7C:
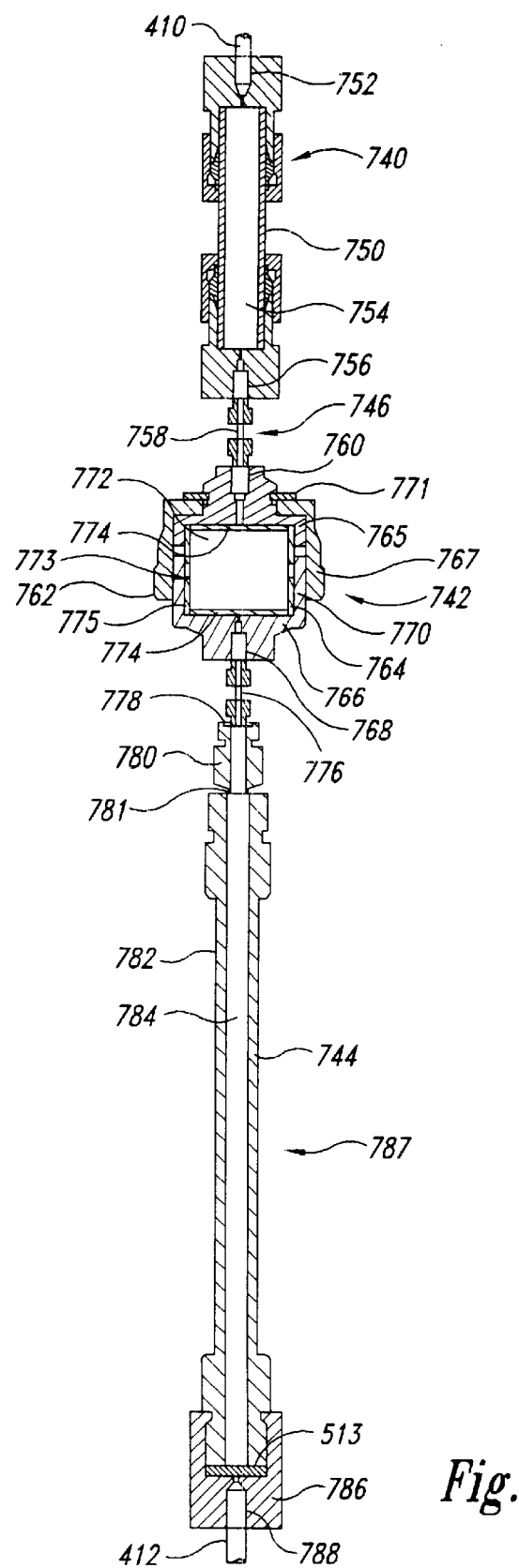
FIG. 7C is a cross-sectional view of another alternative embodiment of a chromatography column according to the invention.

In another embodiment of the present invention shown in FIG. 7C, the column 32 is a staged column assembly having a dilution column 740, a loading column 742, and a separation column 744 spaced apart from each other. The dilution, loading and separation columns 740, 742, and 744 are connected in series by sections of small-bore tubing 746. The dilution column 740 has a dilution chamber body 750 with a top port 752 that receives the inlet tube 410. The inlet port 752 is in fluid communication with a dilution chamber 754 within the dilution body 750, so the sample flows from the inlet tube 410, through the top port 752, and into the dilution chamber 754. The dilution chamber 754 can be empty, or in alternate embodiments, can contain inert media, such as plastic or stainless steel beads. The beads facilitate dilution of the sample flow as it enters the dilution chamber 754. The bottom of the dilution chamber body 750 has an outlet port 756 in fluid communication with the dilution chamber 754. The outlet port 756 is connected to an upper section 758 of the small bore tubing 746 to direct the sample flow out of the dilution column 740. In the illustrated embodiment, the small bore tubing 746 is HPLC tubing having an inner diameter of approximately 0.010 inches, although other tubing can be used.

The upper section 758 of the tubing 746 is connected to an inlet port 760 in the loading body 762 of the loading column 742. The inlet port 760 is in fluid communication with a loading chamber 764 formed within the loading body 762. The loading body 762 is formed by an upper section 765 and a lower section 766 securely held together in axial alignment by a threaded top cap 767. The upper section 765 has the inlet port 760 and the lower section 766 has an outlet port 768 both in fluid communication with the loading chamber 764. The top cap 767 extends over the upper section 765 and internal threads 769 on the top cap screw onto external threads 770 on the lower section 766. A locking ring 771 snaps onto the loading body's upper section 765 over the top cap 767 to lock the top cap in place on the upper section.

The loading chamber 764 contains a selected stationary phase material, such as cyano, or other selected material, that defines a column bed 772. In the illustrated embodiment, the column bed 772 is contained in a guard column cartridge 773 having a shell portion 775 that encases the column bed. Frits 774 are contained in the guard column cartridge 773 on the top and bottom of the column bed 772. The frits 774 are positioned so the sample passes through them as the sample flows through the loading chamber 764 to the outlet port 768. In alternate embodiments, the loading column 742 does not use the guard column cartridge 773. The column bed 772 is packed directly into the loading chamber in 764 and the frits 774 are positioned on the top and bottom of the column bed.

The loading chamber 764 has a volume defined by the diameter and the length that contains a selected volume of the packing material to provide a vertical absorption profile that allows the full sample to be loaded into the loading column 742. The loading chamber's length, however, is insufficient to chromatographically separate the sample. As a result, the loading chamber 764 can receive large samples and spatially distribute the sample across a larger horizontal plane so as to separate the sample from noncompatible loading solvent.

The outlet port 768 of the loading body 762 is connected to a lower section 776 of the small bore tubing 746 that carries the sample flow away from loading column 742. The tubing's lower section 776 is connected to an inlet port 778 in a filter 780. The filter 780 is connected to an inlet port 781 in a separation body of the separation column 744. In an alternative embodiment, the filter 780 is not used, so the tubing's lower section 776 is connected directly to the separation body's inlet port 778.

The separation body 782 has an elongated separation chamber 784 in fluid communication with the inlet port 781 to receive the sample flow. The separation chamber 784 contains a selected separation media forming the column bed 787 through which the sample flow travels and wherein the sample's components are chromatographically separated. The separation chamber 784 has a diameter that is approximately ½ or less than the diameter of loading chamber 764, and a length that is two or more times the loading chamber's length. The sample flow rate is determined by the diameter of the separation chamber 784. The separation chamber 784 of the illustrated embodiment has a cylindrical shape with a substantially continuous cross-sectional area along it length. Alternate embodiments can have a separation chamber 784 that tapers to a smaller diameter at its bottom end.

The bottom end of the separation body 782 is connected to a bottom end cap 786 with an outlet port 788 therein in fluid connection with the separation chamber 784. The outlet port 788 is connected to the outlet tube 412 so as to receive the separated sample flow exiting the separation column 782.

The staged column assembly utilizes the benefit of the large diameter loading column 742 that can handle increased solvent loading, and the smaller diameter separation column 744 that allows for the desired high-volume throughput while achieving the selected chromatographic separation. Accordingly, a large bore column is not needed to achieve the desired separation results.

Figure 7D:
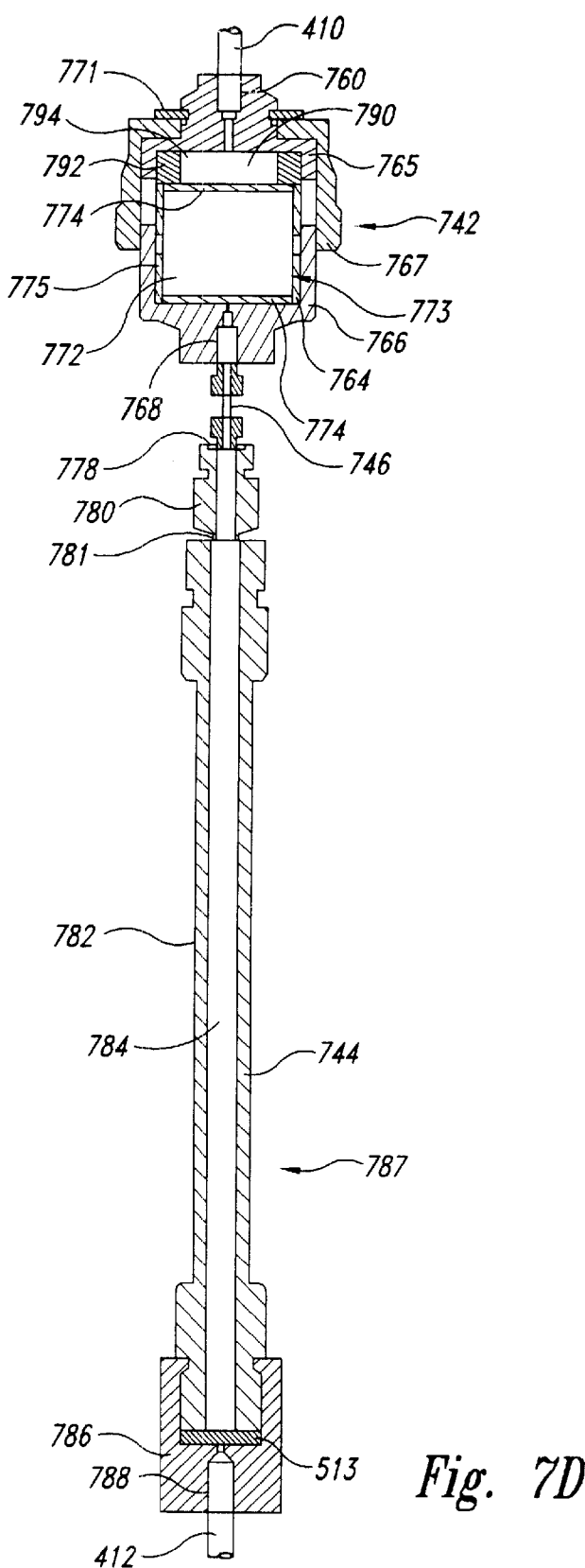
FIG. 7D is a cross-sectional view of another alternate embodiment of a chromatography column according to the invention.

In another alternate embodiment illustrated in FIG. 7D, the column 32 is a staged column assembly similar to the embodiment discussed above and illustrated in FIG. 7C, except the assembly does not have a dilution chamber spaced apart from the loading column. The dilution chamber 790 is provided in the loading column 742. The loading column 742 is connected at its inlet port 760 to the inlet tube 410. The loading column 742 contains an annular spacer 792 sandwiched between the loading body's upper section 765 and the top of the guard column cartridge 773. The annular spacer 792 has an open center area 794 in fluid communication with the inlet port 760 and the guard column cartridge 773 with the column bed 772 therein. The spacer's open center area 794 defines the dilution chamber 790 that receives the sample flow before the sample flow is loaded onto the column bed 772. Accordingly, the dilution chamber 790 and loading chamber 764 are integrally connected in the same stage of the stage column assembly. In the illustrated embodiment, the dilution chamber 790 is empty so as to form a void above the loading chamber 764. In an alternate embodiment, inert beads or other material can be contained in the dilution chamber 790.

In this alternate embodiment, the loading chamber 764 contains selected stationary phase material forming the column bed 772 within the guard column cartridge 773, as discussed above, and the frits 774 sandwich the column bed therebetween. In an alternate embodiment, the guard column cartridge 773 is not used and the column bed 772 and frits 774 are packed directly in the loading chamber 764.

The loading body's lower section 766 has the outlet port 768 as discussed above connected to a segment of the small bore HPLC tubing 746 receives the sample flow from the loading chamber 764. The small bore tubing 746 is connected to the inlet port 778 of the filter 780 as discussed above in connection with the embodiment illustrated in FIG. 7C.

Figure 8A:
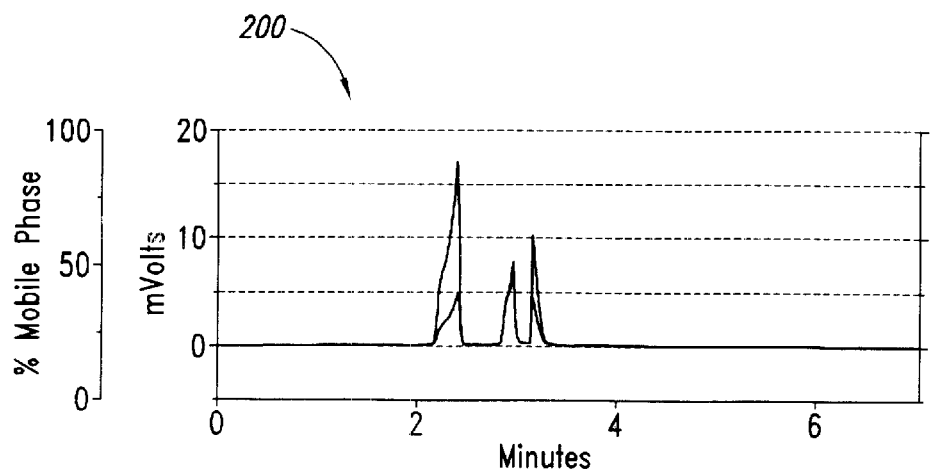
FIGS. 8A–C show results of three chromatographic runs showing the improvement over prior art.
Figure 8B:
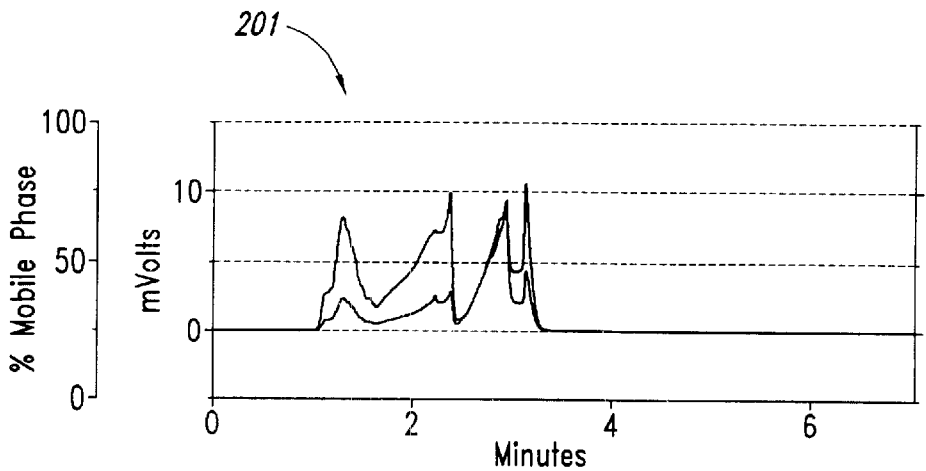
Figure 8C:
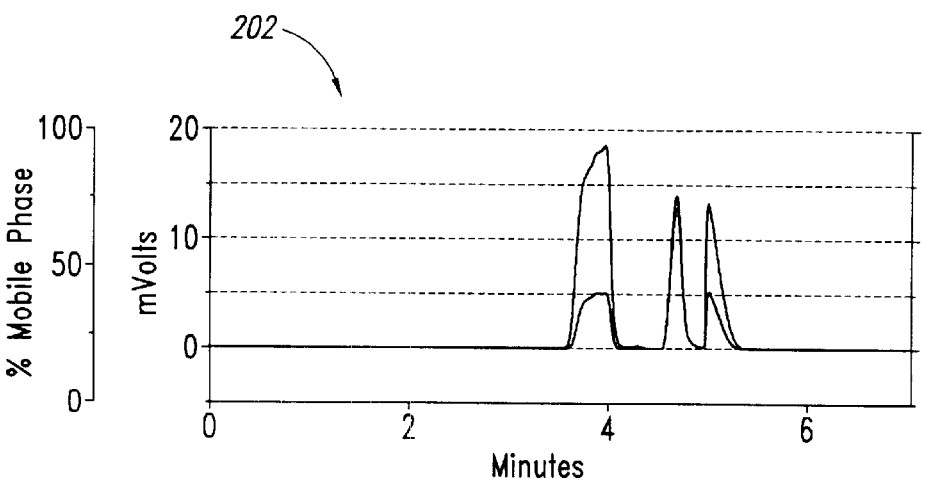

FIGS. 8A–C show graphical results from three chromotographic runs showing improvement over the prior art provided by the column 32 in accordance with the present invention. All three chromotographic runs were injected with the same mass loading of a three-compound mixture and run under the same chromatographic conditions. Run 200 (FIG. 8A) shows the separation results using a single prior art column injected with a small volume solvent mixture. Run 201 (FIG. 8B) shows the separation results using the same prior art single column as in run 200, wherein the prior art column was injected with a large volume solvent mixture. Run 202 (FIG. 8C) shows the separation results using a two-part column 32 in accordance with an embodiment of the present invention as discussed above. Run 202 was injected with the same large volume solvent mixture as run 201.

The first portions of the column 32 (e.g., the loading and transition portions) have a larger inner diameter than the column'second portion (the separation region) and a shorter length than the column'second portion. Accordingly, the column 32 in accordance with the present invention can handle large volume solvent mixtures with multiple compounds and provide highly accurate separation and detection of the different compounds, such as by use of a mass spectrometer or the like. This accuracy in conjunction with corresponding speed for handling large volume solvent mixtures with multiple compounds provides a faster and more efficient processing capability.

Referring again to FIG. 3, the sample flow 31 exits the SFC column 32, flows through another heat exchanger 47, and flows to a detector 34. The detector 34 is adapted to detect the different components or peaks in the sample flow 31 that have been separated from each other by the SFC column 32. In the illustrated embodiment, the detectors 34 are ultraviolet light (UV) detectors. While UV detectors are used in the illustrated embodiment, other detectors can be used, such as infrared (IR) detectors or any other suitable detector capable of identifying a peak within the sample flow 31.

Each detector 34 is coupled to the common computer controller 18. When the detector 34 identifies a peak, the detector provides a signal to the computer controller 18 indicating the peak. Because the sample flow rate is known in each channel 14, the computer controller 18 can calculate the location of each peak within each channel 14 as the sample flow 31 moves through the channel. As an example, when two peaks are detected in the same sample flow 31, the computer controller 18 calculates and monitors where those peaks are within the channel 14. The computer controller 18 also calculates where the peaks are relative to each other during the entire purification process.

As the sample flow 31 moves through the purification channel, it is in a vaporous state. After the sample flow 31 exits the detector 34, additional solvent, referred to as makeup solvent 49, is added to the sample flow as needed to increase the volume of liquid in the sample flow to facilitate transport of the sample to the fraction collector assembly (discussed below). The makeup solvent 49 is pumped from a solvent container by solvent pumps 51 into the respective purification channel 14. The solvent container and the solvent pumps 51 are each coupled to the computer controller 18 so the computer controller can monitor the solvent volumes used and can control the solvent pumps as necessary for the selected purification run. The computer controller 18 also monitors the amount of makeup solvent 49 needed within the purification channel during a run, so it can detect if a potential problem arises, and can provide an alarm or other warning to an operator of the system.

After any of the makeup solvent 49 is added to the sample flow 31, the sample flow passes through a back pressure regulator module 53 in a back pressure regulator assembly 55. The back pressure regulator module 53 detects and controls the back pressure within the channel 14 to maintain the desired pressure within the channel.

Figure 9:
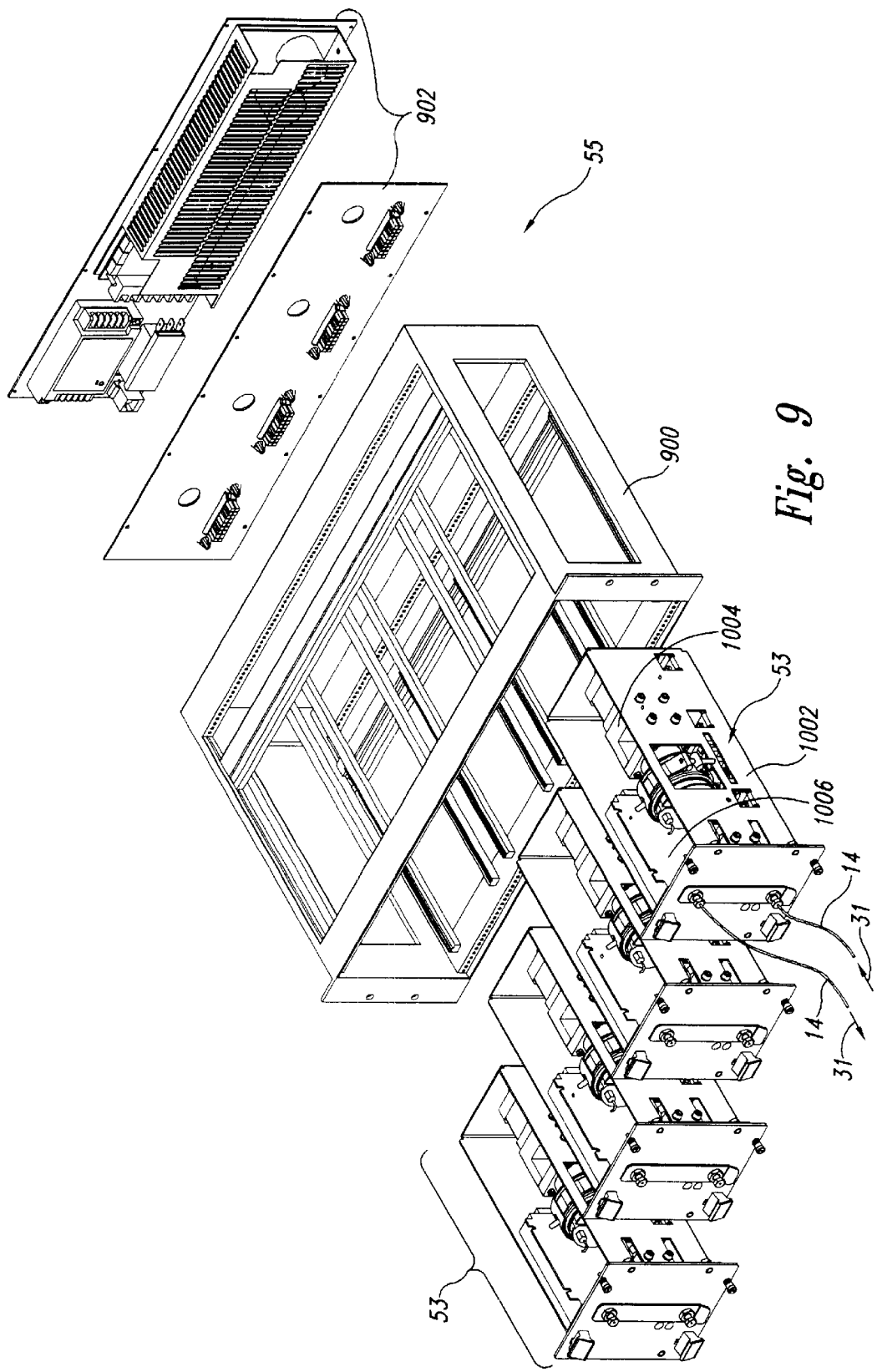
FIG. 9 is an enlarged exploded isometric view of a back pressure regulator assembly from the purification system of FIG. 3.

As best seen in FIG. 9, the back pressure regulator assembly 55 includes a housing 900 that removably retains four back pressure regulator modules 53, one for each purification channel 14. The assembly 55 also includes a communication panel 902 to which the back pressure regulator modules 53 attach for communication to and from the computer controller 18 (FIG. 3). The modules 53 plug into the housing 900 and onto the communication panel 902. Accordingly, if a new or substitute module 53 is needed in the purification system, it can be installed quickly and easily upon unplugging one module and plugging in the replacement module.

Figure 10:
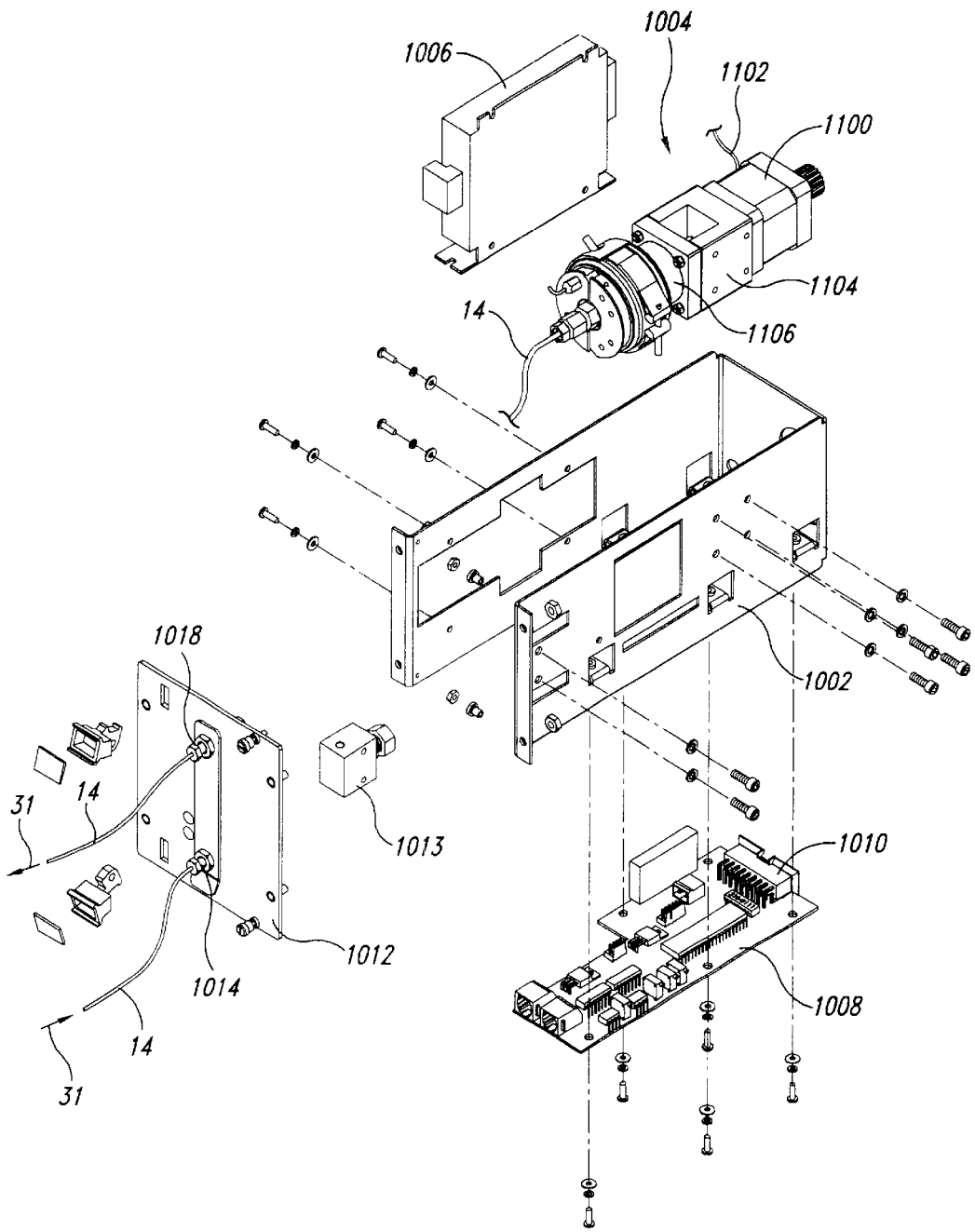
FIG. 10 is an enlarged exploded isometric view of a back pressure regulator module from the assembly of FIG. 9.

As best seen in FIG. 10, the pressure regulator module 53 includes a housing 1002 that contains and protects a regulator assembly 1004. The is regulator assembly 1004 controls the back pressure in the sample flow as it moves through the respective purification channel 14. The regulator assembly 1004 is electrically connected to a stepper motor controller 1006 which activates and adjusts the regulator assembly as needed during a purification run. The stepper motor controller 1006 is connected to a printed circuit board 1008 which also attaches to the housing 1002. The printed circuit board 1008 includes a plurality of connectors 1010 that releasably plug into the communication panel 902 (FIG. 9) of the regulator assembly. Accordingly, communication to and from the computer controller 18 is provided to the pressure regulator module 53 through the printed circuit board and to the regulator assembly 1004 via the stepper motor controller 1006.

The pressure regulator module 53 also includes a front faceplate 1012 that mounts to the housing 1002. The front faceplate 1012 has an inlet port 1014 into which the tubing of the purification channel extends so as to allow the sample flow 31 to pass into the pressure regulator module 53. The sample flow passes through a pressure sensor 1013, which is also coupled to the printed circuit board 1008, so as to identify the sample flow's pressure. After the sample flow 31 enters the regulator assembly 1004 and the sample flow's pressure is modified as needed, as discussed in greater detail below, the sample flow exits the pressure regulator module 53 through an outlet port 1018 on the front faceplate 1012.

Figure 11:
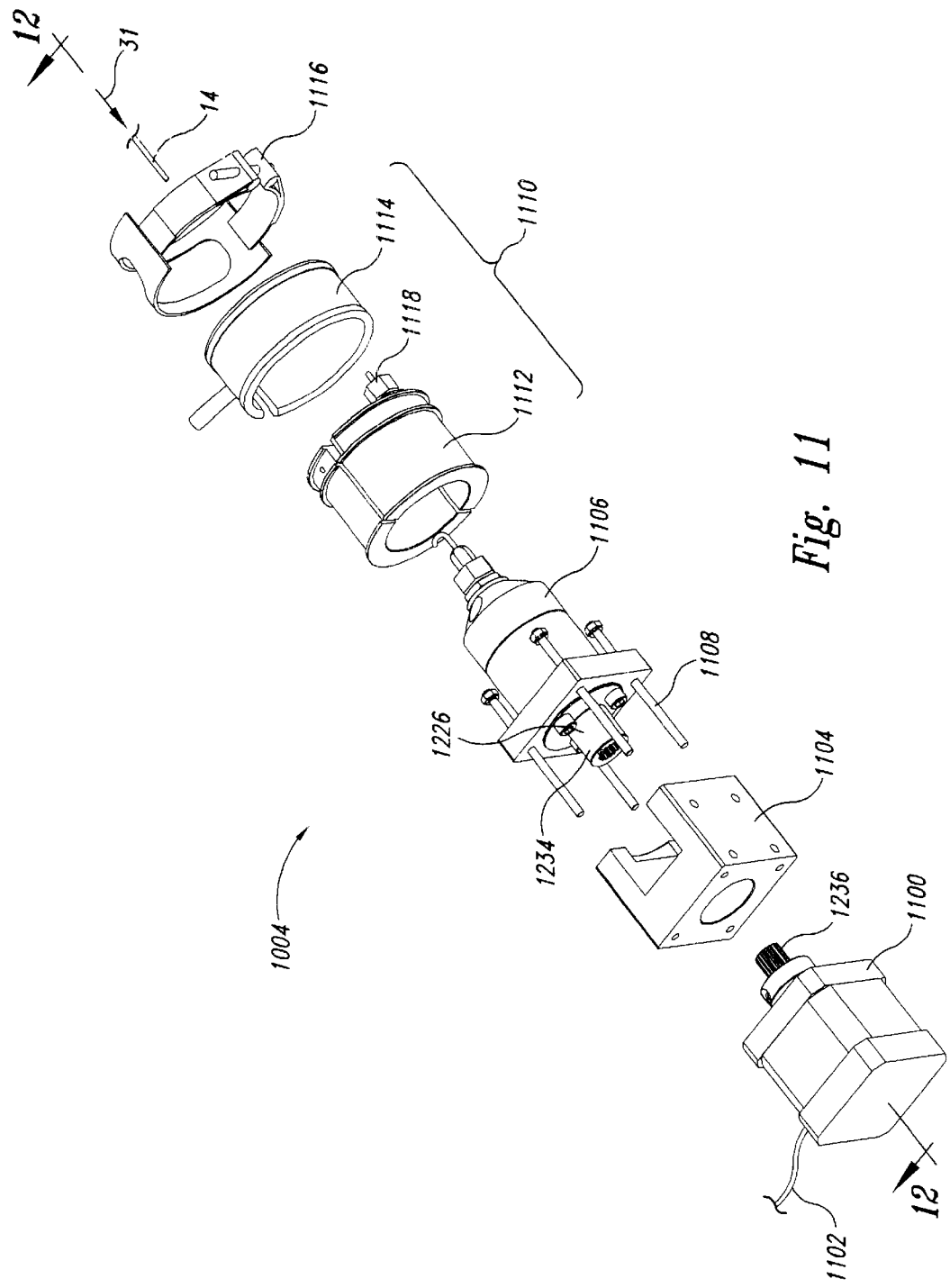
FIG. 11 is an enlarged isometric view of a regulator/motor assembly of the back pressure regulator module of FIG. 10.
Figure 12:
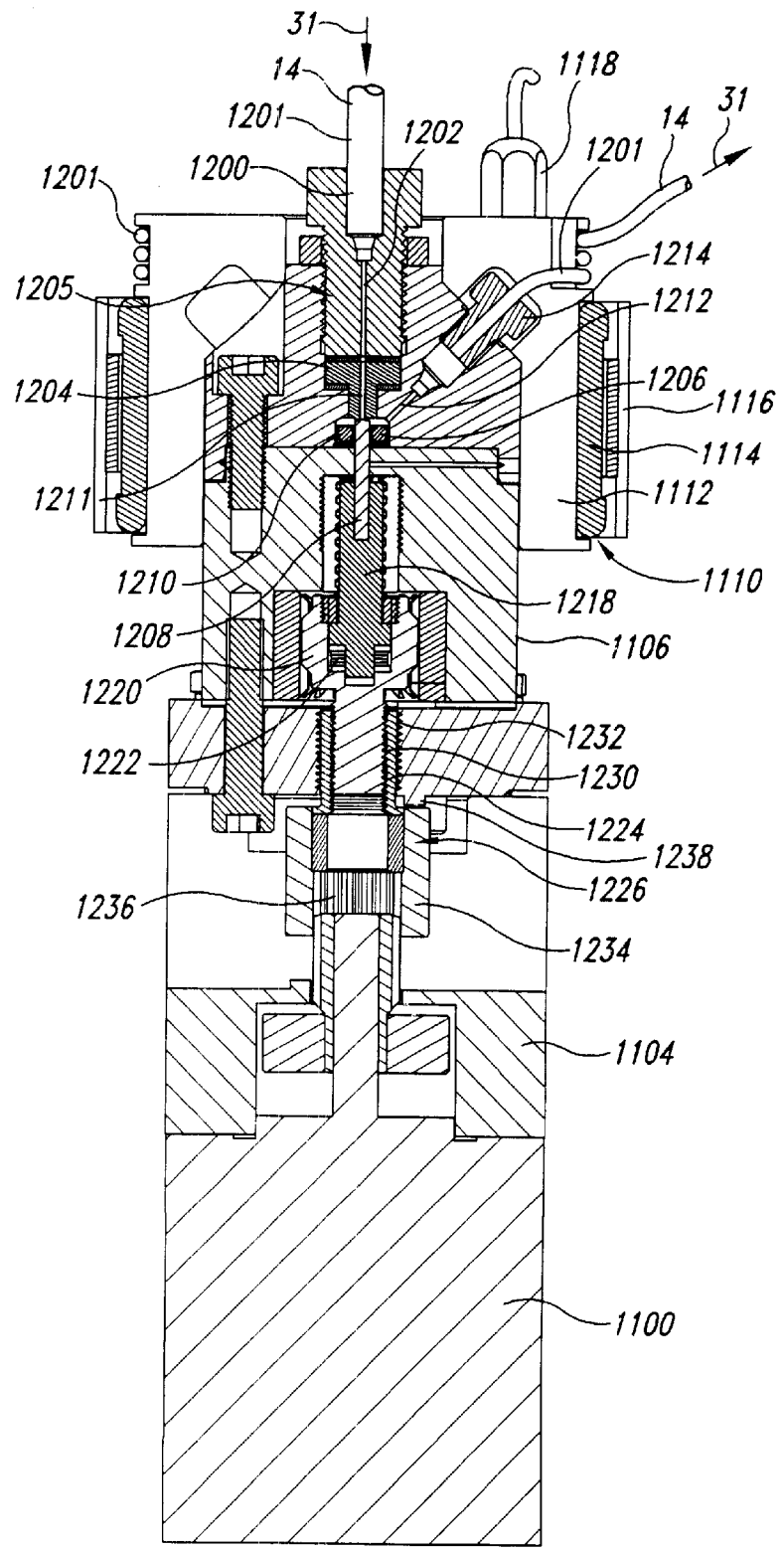
FIG. 12 is an enlarged cross-sectional view of the regulator assembly taken substantially along line 12—12 of FIG. 11.

As best seen in FIGS. 11 and 12, the regulator assembly 1004 includes a stepper motor 1100 having wiring 1102 that connects to the stepper motor controller 1006 (FIG. 10). The stepper motor 1100 is connected to a motor mount 1104 that interconnects the stepper motor to a back pressure regulator 1106. The back pressure regulator 1106 is securely retained to the stepper motor 1100 by a plurality of mounting screws 1108 that extend through the motor mount 1104 and screw into the housing of the stepper motor 1100.

The regulator assembly 1004 also includes a heater 1110 adapted to heat the sample flow 31 within the purification channel's tubing so as to prevent formation of ice crystals or the like that may occur as a result of pressure differentials occurring across the pressure regulator. The heater 1110 includes a heat transfer body 1112 that extends over the back pressure regulator 1106 and a heater band 1114 clamped onto the heat transfer body by a band clamp 1116. The heater band 1114 is coupled to the computer controller 18 to allow the heater band to regulate its temperature to provide different heating configurations to the back pressure regulator during a purification run. The heat transfer body 1112 includes a temperature sensor 1118 that monitors the temperature of the heat transfer body during the purification run. The temperature sensor 1118 is coupled to the computer controller 18 (FIG. 3) so the computer controller can regulate the heat provided from the heater band 1114 as needed during operation of the regulator assembly 1004.

As best seen in FIG. 12, the regulator 1106 has an inlet port 1200 that receives the purification tube 1201 carrying the sample flow 31. The inlet port 1200 has an inlet channel 1202 that communicates with a nozzle 1204 positioned below the inlet port. The nozzle 1204 in the illustrated embodiment is a ceramic component having a diamond coating so as to provide an extremely hard and durable nozzle within the regulator. The nozzle 1204 is exposed to very harsh conditions, including caustic solvents and pressures of approximately 2000 psi or greater. The inlet port 1200 is threadably connected to the nozzle retainer 1205 so the inlet port is easily removable to provide access to the nozzle 1204 if replacement of a nozzle is necessary.

The nozzle 1204 includes an inlet channel 1211 extending therethrough that communicates with a very small chamber that receives the sample flow 31 from the nozzle's inlet channel. The lower end of the inlet channel 1211 forms a nozzle orifice through which the sample flow passes. A stem 1208 positioned below the nozzle 1204 extends through a seal 1210, into the small chamber 1206, and terminates immediately adjacent to the nozzle orifice at the lower end of the inlet channel 1211. The stem 1208 is moveable relative to the nozzle orifice so as to adjustably close the flow path through the regulator 1206. In the illustrated embodiment, the stem 1208 is a sapphire stem. In alternate embodiments, the stem 1208 can be made of other very hard materials, such as diamond, ruby or the like. The stem 1208 is movable relative to the nozzle 1204 to adjust the opening size so as to regulate the pressure of the sample flow 31.

The sample flow 31 moves from the nozzle 1204 through the orifice and into an outlet channel 1212 that is in fluid communication with the small chamber 1206. The outlet channel 1212 extends through an outlet port 1214 that receives the exit tube 1201 therein so as to carry the sample flow 31 out of the regulator 1106. The exit tube 1201 extends from the outlet port 1214 and wraps around the heat transfer body 1112 approximately two times so the exit tube is heated, thereby preventing the formation of ice crystals within the purification tube and condensation on the outside of the exit tube. The purification tube 1201 then extends from the heat transfer body 1112 away from the regulator assembly and to the outlet port 1018 on the regulator module's faceplate 1012 (FIG. 10) as discussed above.

In the illustrated embodiment, the stem 1208 is a sapphire stem having hardness characteristics suitable for use in the high pressure and harsh environment within the regulator assembly 1004. The sapphire stem 1208 is connected at its lower end to a rod 1218 movably positioned within a holding member 1220 having a threaded lower end. The holding member 1220 contains a biasing member 1222, such as Bellville washers, wave washers, or the like, that bias the rod 1218 and the stem 1208 toward the nozzle 1204. In the event the stem 1208 directly engages the nozzle 1204 or is subjected to an extremely high pressure pulse, the biasing member 1222 will compress so as to avoid damaging the sapphire stem 1208 or the nozzle 1204 during operation. The biasing member 1222, however, has a sufficient spring stiffness so it is not compressed during normal pressures of the sample flow within the tubing of the purification channel 14 during a purification run.

Adjustment of the regulator assembly 1106 is provided by dual concentric screws that move the stem 1208 relative to the nozzle 1204. As best to seen in FIG. 12, the holding member 1220 is threaded into internal threads 1230 formed in a shaft 1224 of an adjustment screw 1226. In the illustrated embodiment, the internal threads 1230 have a pitch of 28 threads per inch (tpi). The adjustment screw's haft 1224 also has external threads 1232 that screw into a threaded aperture in the regulator body 1106. In the illustrated embodiment, the external threads 1232 have a pitch of 27 tpi. Accordingly, the external threads 1232 of the adjustment screw 1226 have a thread pitch different than the pitch value of the internal threads 1230. The internal and external threads 1230 and 1232 are both right-handed pitch threads oriented in opposing directions so as to form the dual concentric adjustment screw configuration for attenuated movement of the stem 1208 relative to the nozzle 1204 for each turn of the adjustment screw.

The adjustment screw 1226 has an internal driving spline 1234 that securely engages a drive spline 1236 on the stepper motor 1100. The drive spline 1236 is press fit into the internal driving spline 1234. When the stepper motor 1100 is activated by the computer controller 18 (not shown), the driving spline 1236 rotates, thereby rotating the adjustment screw 1226. As the adjustment screw 1226 rotates one revolution, the dual concentric screw configuration counteracts the range of motion of the holding member 1228, and thus the stem 1208. As an example, if the stepper motor 1100 rotates the adjustment screw one full revolution, the holding member 1220 moves only one pitch value because of the pitch differentiation between the internal and external threads 1230 and 1232.

In one embodiment one revolution of the adjustment screw along the external threads 1232 would move the adjustment screw 1226 and the holding member 1220 approximately 0.0373 inches. The internal threads 1230, however, move in the opposite direction approximately 0.03571 inches, resulting in a net movement of approximately 0.0013 inches. Accordingly, the dual concentric screw configuration within the regulator 1106 provides for extremely accurate and fine adjustments of the stem 1208 relative to the nozzle 1204 to closely control pressure regulation within the sample flow 31 as it passes through the back pressure regulator assembly 1004.

The back pressure regulator 1004 is formed with a minimum amount of dead volume and unswept volume within the purification channel extending therethrough to prevent or minimize the risk of cross contamination between purification runs for different samples. The back pressure regulator assembly is constructed with extremely durable components that will withstand the harsh environments experienced during the purification run at very high pressures, while providing sufficient safety characteristics to avoid damaging the back pressure regulator in the event of pressure spikes or the like.

In one embodiment, the stepper motor includes a rotational stop 1238 that prevents travel of the drive spline 1236 and, thus, the adjustment screw 1226 past a selected position relative to the regulator. The travel stop 1238 is positioned to block the stepper motor from driving the sapphire stem 1208 too far relative to the nozzle 1204, thereby preventing damage from overdriving from the stepper motor and crushing the sapphire stem against the nozzle.

The illustrated embodiment of the purification system utilizes the regulator assembly with the dual concentric screw configuration controlled by the computer controller 18. In alternate embodiments, the pressure regulator assembly 53 can be a stand alone regulator with selected control mechanisms.

As best seen in FIG. 3, the sample flow 31 travels from tie pressure regulator assembly 55 to the microsample valve 38. The microsample valve 38 is operatively connected to the computer controller 18 and is activated by the computer controller when a peak in the sample flow 31 is moving past the microsample valve. Upon activation, the microsample valve 38 diverts a sampling from the sample flow 31 and directs it to the mass spectrometer 16 for analysis. The remaining portion of the sample flow 31 continues along the flow path of the respective channel 14 substantially uninterrupted. Each microsample valve 38 is activated so the sampling contains a selected portion of just the peak. The mass spectrometer 16 analyzes the sampling and determines whether the peak is a target compound or not.

As the four sample flows 331 moves simultaneously through the respective channels 14 and through the detectors 34, the peaks from the four channels will likely occur at separate times during the sample runs. Accordingly, the mass spectrometer 16 usually receives the samplings from the four channels with some time between the samplings. In some cases, however, two or more detectors 34 may detect a peak in its sample flow at the same time or at overlapping times during the sample run. The computer controller 18 is programmed with an analysis priority protocol that controls the activation sequence of the microsample valve 38 when peaks in the different channels 14 occur at the same time or overlapping times. Accordingly, the priority protocol controls the timing of when the samplings of the peaks are diverted to the mass spectrometer 16, so each peak can be analyzed separately by the same analyzer. In one embodiment, when a peak from separate channels 14 are detected simultaneously, the computer controller 18 activates the microsample valves 38 at different times so samplings of the respective peaks are sequentially directed to the mass spectrometer 16. Activation of each microsample valve 38 can be controlled by revising the computer controller's analysis priority protocol to provide sequential sampling.

Figure 13:
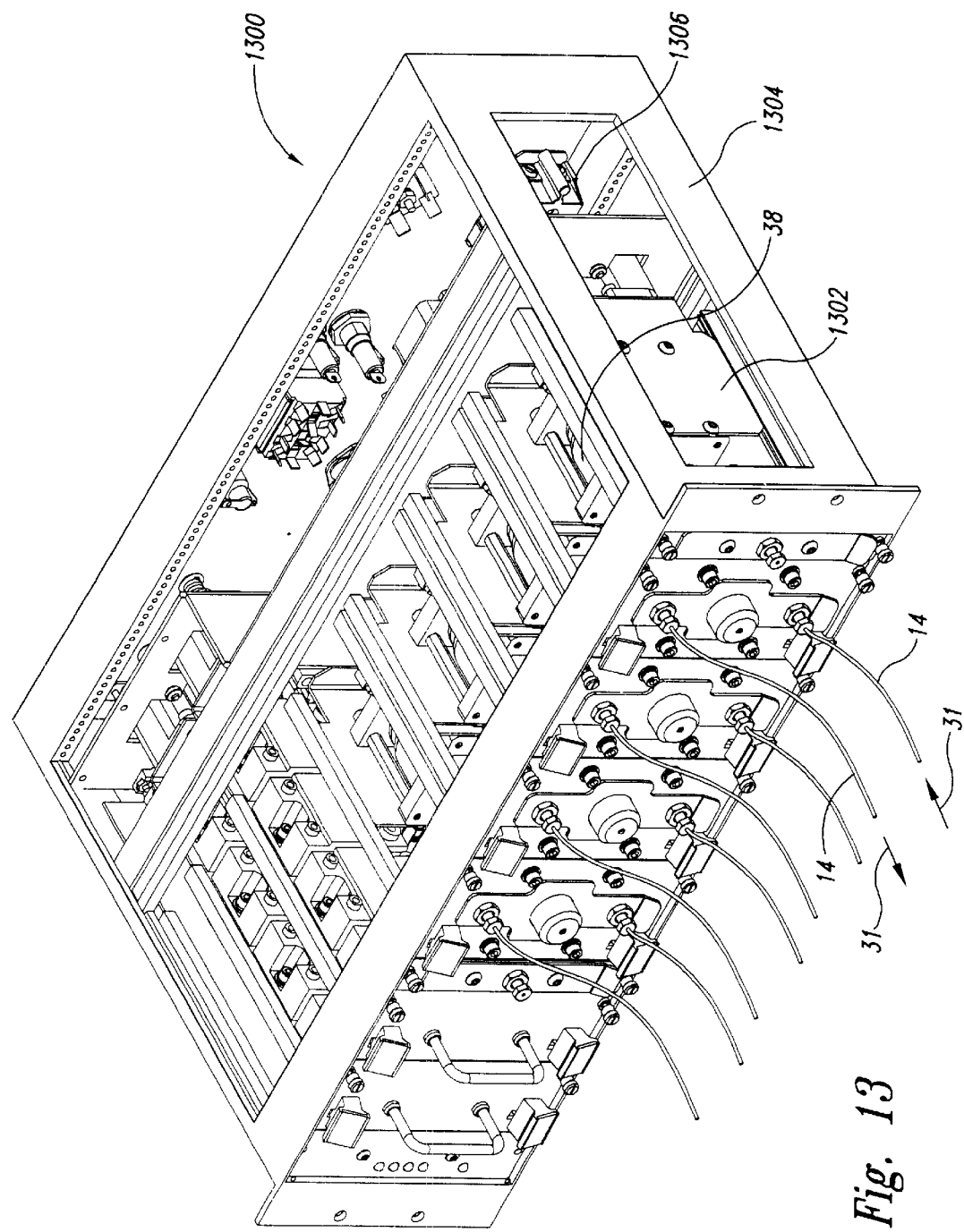
FIG. 13 is an enlarged isometric view of a microsample valve lo assembly from the purification system of FIG. 3.

As best seen in FIG. 13, the four microsample valves 38 are part of a microsample valve assembly 1300 that has four valve modules 1302. Each valve module 1302 contains a microsample valve 38 for its respective purification channel 14. The valve modules 1302 are removably received by a housing 1304 and plug into connectors coupled to a communication panel 1306. The communication panel 1306 is, in turn, coupled to the computer controller 18 (not shown), so the computer controller can control the activation of each microsample valve 38.

Figure 14A:
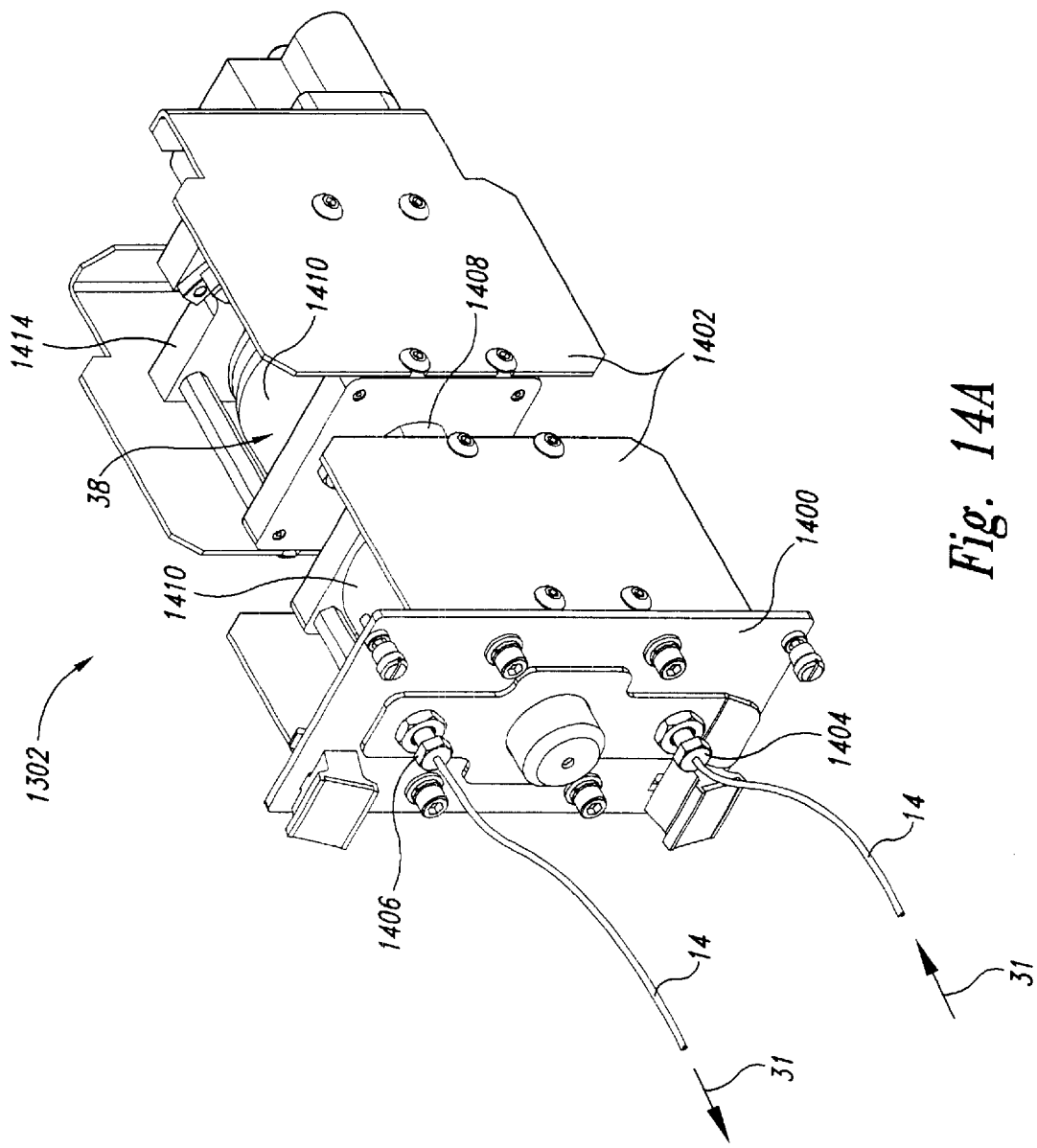
FIG. 14A is an isometric view of a microsample valve from the assembly of FIG. 13.
Figure 14B:
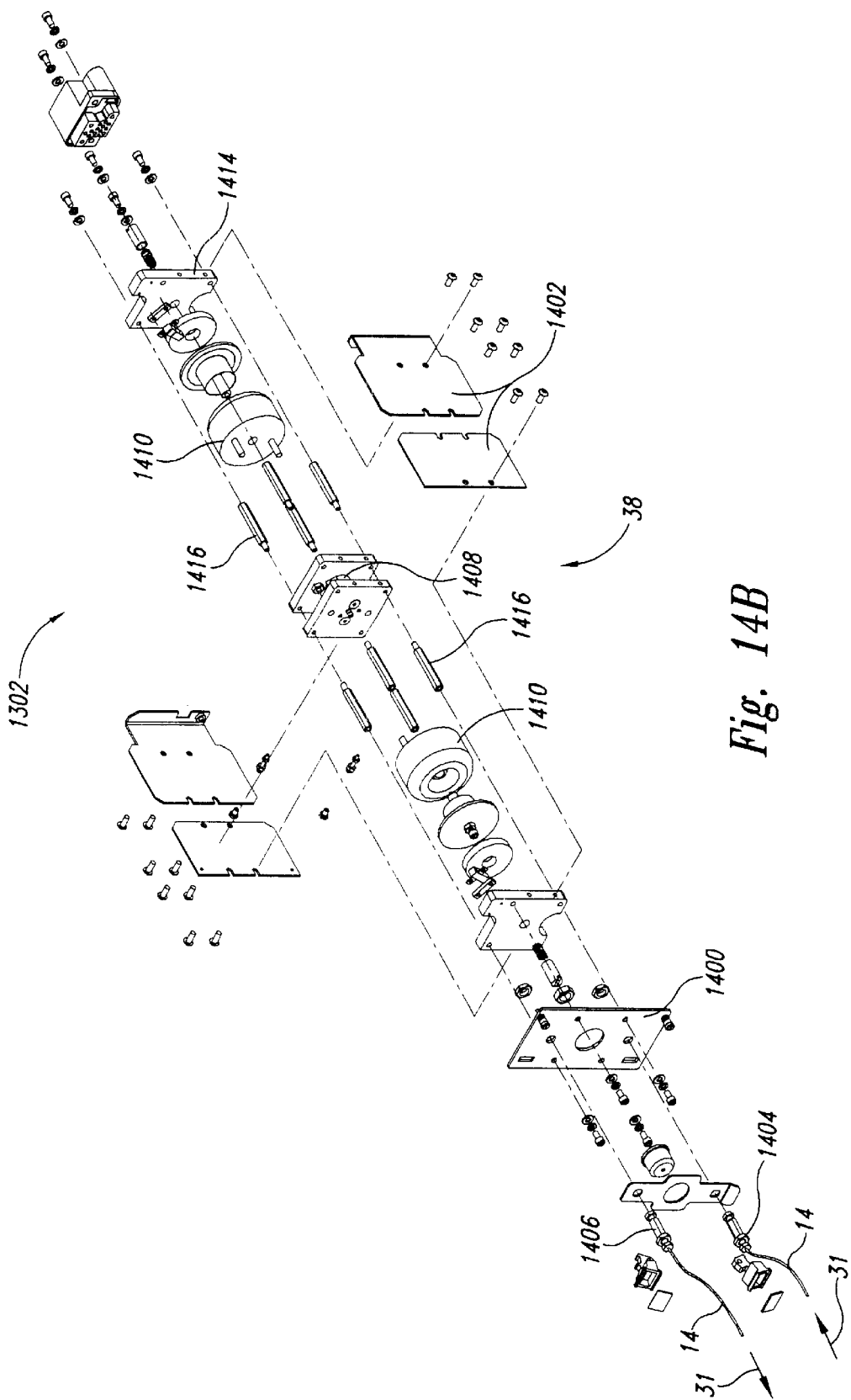
FIG. 14B is an enlarged, exploded isometric view of a microsample valve from the assembly of FIG. 13.

As best seen in FIGS. 14A and 14B, each valve module 1302 includes a faceplate 1400 and opposing side plates 1402 that securely engage the microsample valve 38. The faceplate 1400 has an inlet port 1404 and an outlet port 1406 that receive the purification channel's tubing and direct the sample flow into and out of the valve module 38.

The microsample valve 38 includes a valve body 1408 positioned between a pair of electromagnetic solenoids 1410. The solenoids 1410 are activatable by the computer controller 18 (not shown) to control activation of the microsample valve, as discussed in detail below. The solenoids 1410 are each sandwiched between the valve body 1408 and outer mounting plates 1414, and mounting screws 1416 secure the outer mounting plates to the valve body.

Figure 15:
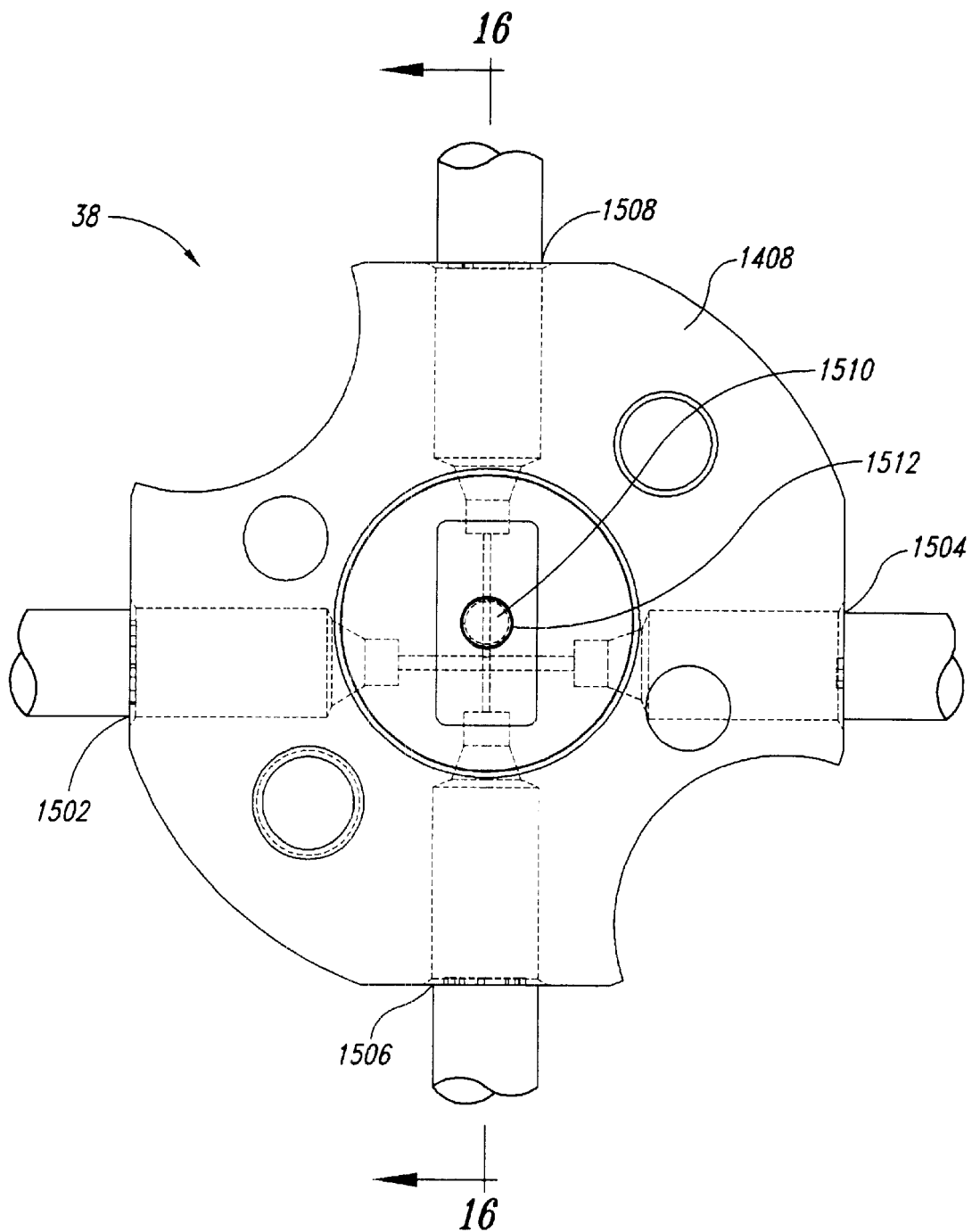
Figure 16:
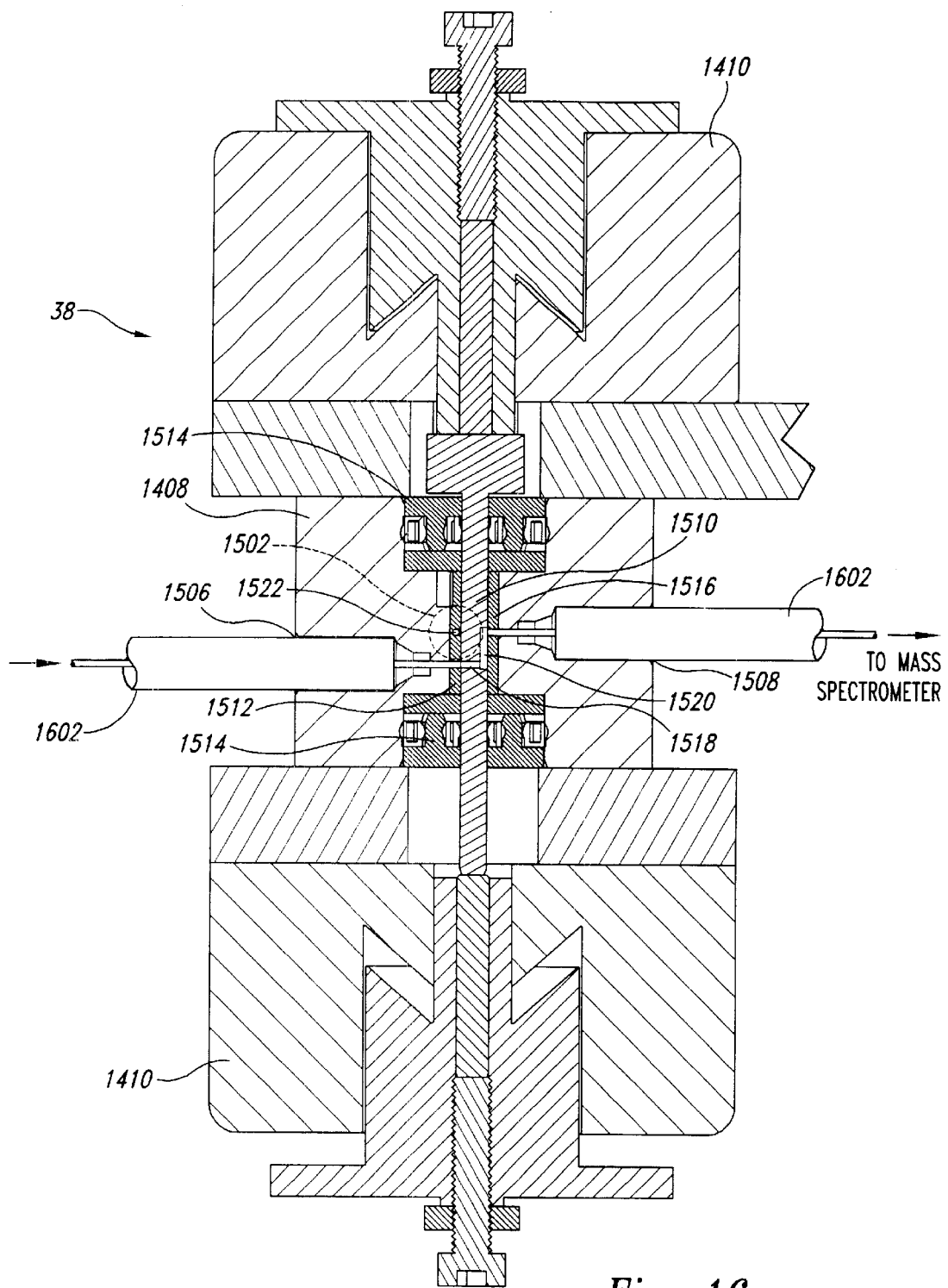
FIG. 16 is an enlarged cross-sectional view taken substantially along line 16—16 of FIG. 14, the microsample valve being shown in a non-sampling position.
Figure 17:
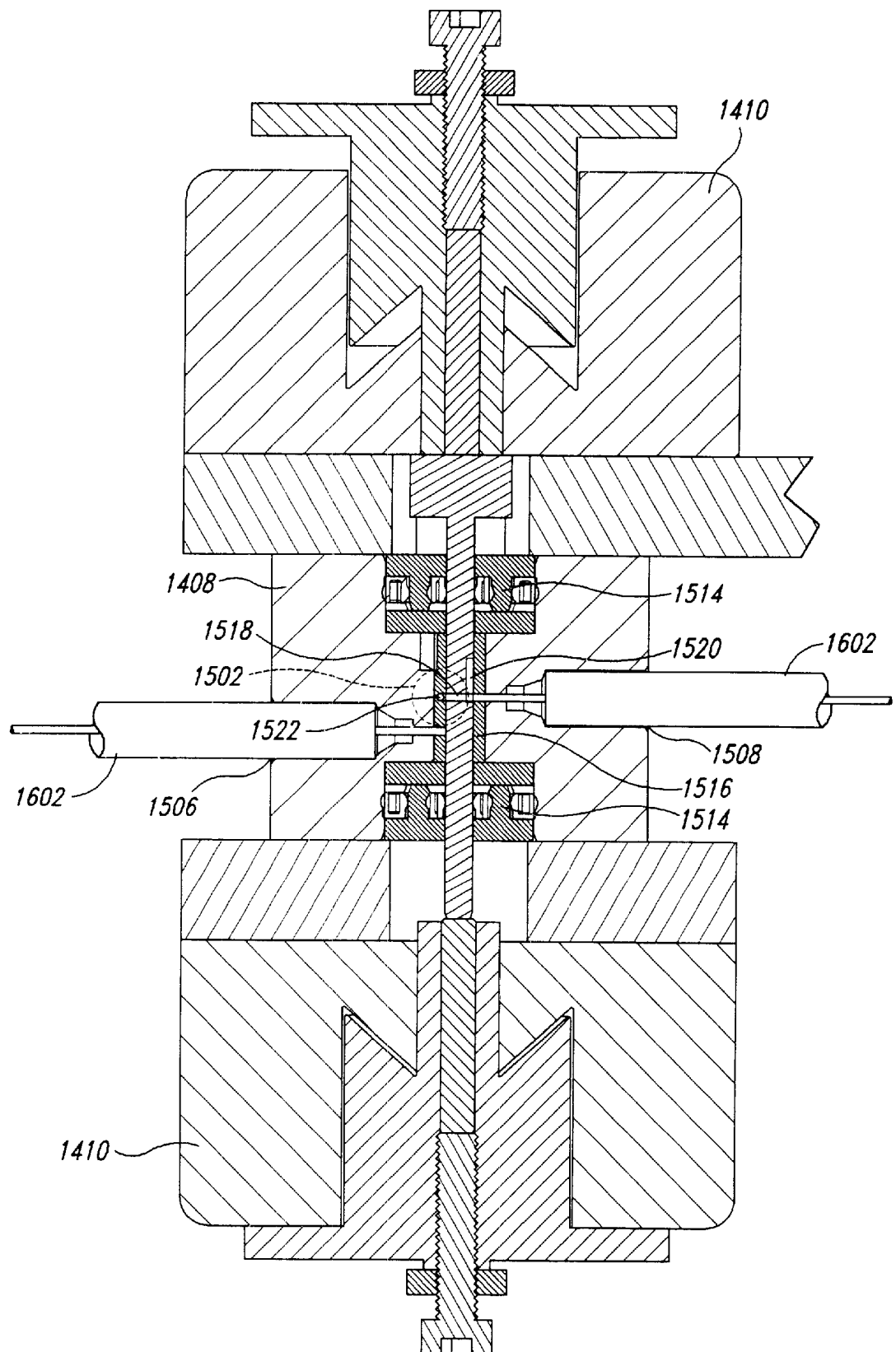
FIG. 17 is an enlarged cross-sectional view taken substantially along line 17—17 of FIG. 14, the microsample valve being shown in a sampling position.

As best seen in FIGS. 15–17, the valve body 1408 has a sample inlet port 1502, a sample outlet port 1504 (FIG. 15), a solvent inlet port 1506, and a flow outlet port 1508. The solvent inlet port 1506 is axially misaligned with the flow outlet port 1508. The flow outlet port 1508 is in fluid communication with the mass spectrometer 16, so fluid exiting the microsample valve 38 through the flow outlet port is carried to the mass spectrometer 16 (FIG. 3). The microsample valve 38 has a stem 1510 slidably disposed within an interior chamber 1512 in the valve body 1408. The stem 1510 slidably extends through the valve body 1408 and is connected at opposite ends to the electromagnetic solenoids 1410. The solenoids 1410 control the stem's axial position within the valve body 1408. The solenoids 1410 are connected to the computer controller 18 (FIG. 3), so the computer controller can control or adjust the stem's axial position. Upper and lower seals 1514 are positioned within the valve body 1408 adjacent to the solenoids 1410, and a center plastic sleeve 1516 extends between the upper and lower seals. The stem 1510 extends through the upper and lower seals 1514 and the plastic sleeve 1516 such that a fluid-tight seal is formed therebetween. In the illustrated embodiment, the stem 1510 is press fit into the plastic sleeve 1516, thereby preventing dead space around the stem.

As best seen in FIGS. 16 and 17, the stem 1510 has a through hole 1518 in fluid communication with the flow outlet port 1508 and to the mass spectrometer 16. The stem 1510 also has an axial groove 1520 on the outflow side of the valve body 1408 and in fluid communication with the flow outlet port 1508. The axial groove 1520 extends upwardly from the through hole 1518, along the stem's surface, and is sized to direct the fluid flow upwardly from the through hole along the groove between the stem's surface and the center plastic sleeve 1516. The through hole 1518 is shaped and sized to allow either a flow of carrier solvent or a sampling of a peak from the sample flow to pass toward the mass spectrometer 16.

Referring now between FIGS. 3, 15 and 16, the solvent inlet port 1506 (FIGS. 15 and 16) is connected to a carrier solvent line 1602 that connects to a carrier solvent source 1604 (FIG. 3) and a carrier solvent pump 1606. The carrier solvent pump 1606 is also coupled to the computer controller 18 that controls the flow of carrier solvent to the microsample valves 38. A substantially continuous flow of carrier solvent is provided to the microsample valves 38 during a purification run. In the illustrated embodiment, the carrier solvent line 1602 connects to all four microsample valves 38 in series, so the carrier solvent will flow through all of the microsample valves and to the mass spectrometer 16. Accordingly, the carrier solvent enters the first microsample valve 38 through the solvent inlet port 1506 (FIGS. 15 and 16), exits through the flow outlet port 1508 (FIG. 16), back into the carrier solvent line 1602, and into the next microsample valve through its solvent inlet port. The flow continues through each microsample valve 38 and then to the mass spectrometer 16.

The microsample valve 38 in each purification channel 14 also has a continuous flow of the sample flow 31 passing through it. The sample flow 31 enters the microsample valve 38 through the sample inlet port 1502 (FIGS. 15 and 16), through a sample line 1522 extending through the valve body 1408 immediately adjacent to the stem 1510, and out through the sample outlet port 1504. Accordingly, the sample flow 31 in the illustrated embodiment is transverse to the flow of the carrier solvent.

When the microsample valve 38 is in a lowered normal position, shown in FIG. 16, the through hole 1518 is below and out of communication with the sample flow 31. The stem 1510 blocks the sample flow 31 from passing through the flow outlet port 1508 to the mass spectrometer 16 (FIG. 3). When the stem 1510 is in the lowered position, a continuous flow of carrier solvent passes into the valve body 1408 through the solvent inlet port 1506, through the through hole 1518, up the axial groove 1520, and out of the valve body 1408 through the flow outlet port 1508 toward the mass spectrometer 16.

During normal use, when a peak has not been identified, the microsample valve 38 remains in this lowered normal position, so only the carrier solvent flows through the microsample valves to the mass spectrometer 16. When the detector 34 (FIG. 3) detects a peak in the sample flow 31 and the computer controller 18 activates the microsample valve 38, the solenoids 1410 immediately move the stem 1510 axially from the lowered position to a raised sampling position, shown in FIG. 17. In this raised sampling position, the through hole 1518 in the stem 1510 is in fluid communication with the sample line 1522 through which the sample flow 31 travels between the sample inlet and outlet ports 1502 and 1504. Accordingly, the flow of carrier solvent is temporarily interrupted and a small sampling of the peak traveling through the sample line 1522 is diverted from the sample line, through-the through hole 1518 to the flow outlet port 1508, and into the carrier line at the location where the carrier solvent flow was interrupted. The sampling then flows to the mass spectrometer 16 (FIG. 3) for analysis.

As the peak is moving past the through hole 1518 at a selected time, as determined by the computer controller 18, the stem 1510 is switched back to the lowered position (FIG. 16). The solenoids 1410 are activated, thereby immediately moving the stem 1510 axially to the lowered position, so the only part of the sample flow 31 received by the mass spectrometer 16 for analysis is the sampling of the peak. When the stem 1510 is returned to the lowered position, the flow of the carrier solvent to the mass spectrometer 16 is resumed. Therefore, the mass spectrometer 16 receives a continuous flow of fluid, and the samplings are effectively inserted as segments of that continuous flow when the microsample valve 38 is activated.

The axial movement of the stem 1510 between the lowered position and the raised sampling position allows for an extremely fast switching between positions, thereby providing for small yet highly accurate samplings of the selected portion of the sample flow. In the illustrated embodiment, the microsample valve 28 is configured to be switched from the normal lowered position, to the raised sampling position and back to the normal lowered position within a time period of approximately 15 to 100 milliseconds, inclusive. In one embodiment the time period is less than 20 milliseconds, so as to divert sample volumes as small as approximately 2 pico liters or less to the mass spectrometer 16. In an alternate embodiment, the microsample valve 28 is configured to be movable from the normal lowered position, to the raised sampling position and back to the normal lowered position in one second or less. This extremely fast switching also minimizes the chance of cross-contamination within the valve body between samplings of a plurality of peaks within the sample flow.

The microsample valve 38 is designed and constructed so the flow paths through the valve body 1408 and the stem 1510 provide virtually no dead space or unswept volumes that could cause cross-contamination between different samples flowing through the microsample valve. Accordingly, the microsample valve 38 allows for very accurate results in the purification process. The microsample valve 38 is also configured to quickly take the small sample portions from the sample flow, thereby minimizing the pressure drop in the sample flow across the microsample valve 38. In the illustrated embodiment, the pressure drop across the microsample valve is less than approximately 50 psi.

As best illustrated in FIG. 3, the sample flow 31 in each channel 14 moves from the microsample valve 38 to a pressure relief valve assembly 41 that controls the pressure within the flow downstream of the microsample valve. In the illustrated embodiment, the pressure relief valve assembly 41 has the same construction as the back pressure regulator assembly 55 discussed above, except that the heaters are not provided on the back pressure regulator valve. In alternate embodiments, the heaters can be used if needed as a result of ice formation or larger pressure drops experienced in the system. In other alternate embodiments, other back pressure regulators can be used, provided they are durable enough and provide sufficient pressure control for the purification valve.

The use of the pressure relief valve 41 allows the flow volume to the analyzer to be very small because of either use of a small bore capillary to the analyzer or an active back-pressure regulator. Accordingly, the pressure differential is reduced and the flow volume to the mass spectrometer 16 is reduced.

The sample flow 31 exits the pressure relief valve assembly 41 and flows to flow directing valves, referred to as a fraction collection valve assemblies with first and second collection valves 40a and 40b for each channel. Each fraction collection valve assembly 40 has, for each channel, one inlet port 42, two outlet ports 44 and 46 for collection, and a waste port 47 the inlet port 42 is coupled to both of the first and second collection valves 40a and 40b, and each outlet port 44 and 46 is connected to a respective one of the first or second collection valves. Each of the first and second collection valves 40a and 40b are also operatively coupled to the computer controller 18. When a portion of the sample flow 31 containing a peak enters the fraction collection valve assembly 40 through the inlet port 42, as identified by the computer controller 18, the computer controller activates the first or second fraction collection valve 40 a and 40b to control whether the peak in the sample flow is directed out of the first outlet port 44 or the second outlet port 46.

If the mass spectrometer 16 determines that the peak is the target compound, the computer controller 18 activates the fraction collection valve 40, so the fraction collection valve moves to a first position. In this position, the sample portion containing the peak is directed out of the fraction collection valve 40 through the first outlet valve 44. The sample portion is directed to a fraction collector assembly 43 and is collected directly into a predetermined location in a selected well of the first receiving microtiter plate 22.

When a portion of a sample flow containing a peak passes through the fraction collection valve 40, and that peak is a crude rather than the target compound, the fraction collection valve is switched to a second position to direct a portion of the sample flow through the second outlet port 46. This portion of the sample flow 31 exits the second outlet port 46, passes through the fraction collection assembly 43 and is collected directly into a selected well of the second receiving microtiter plate 24. When a portion of the sample flow 31 passes through the fraction collection valve and that portion does not contain any peaks, the sample flow passes through the waste outlet 47 and is carried to a waste receptacle 52.

The purification system 10 of the exemplary embodiment allows the purified samples to be automatically dispensed into selected wells of the receiving microtiter plate 22 or 24, where each sample is dispensed into a well having the same relative location in the receiving microtiter plate as the supply microtiter plate well from which the sample was initially drawn to begin the purification run. Therefore, the purified target compound is deposited directly into a well having a one-to-one corresponding well address as the original sample well. Similarly, the purified reaction by-products are deposited directly into a well having a corresponding well address and the second receiving microtiter plate, so the reaction by-products are collected separately from the purified target compounds. This direct depositing of the target compounds into a selected microtiter plate well avoids further processing and formatting before the purified target compounds are put into microtiter plates. Accordingly, the efficiency of the purification process is increased and the time and cost requirements are decreased.

This purification system 10 of the illustrated embodiment results in the collection of purified compounds having an 85% purity or better. It is preferred, of course, to provide samples having purity as close to 100% pure as possible. Upon collection of the purified target compounds in the receiving microtiter plate 22, these purified target compounds are ready for a screening process or other selected process.

Figure 20:
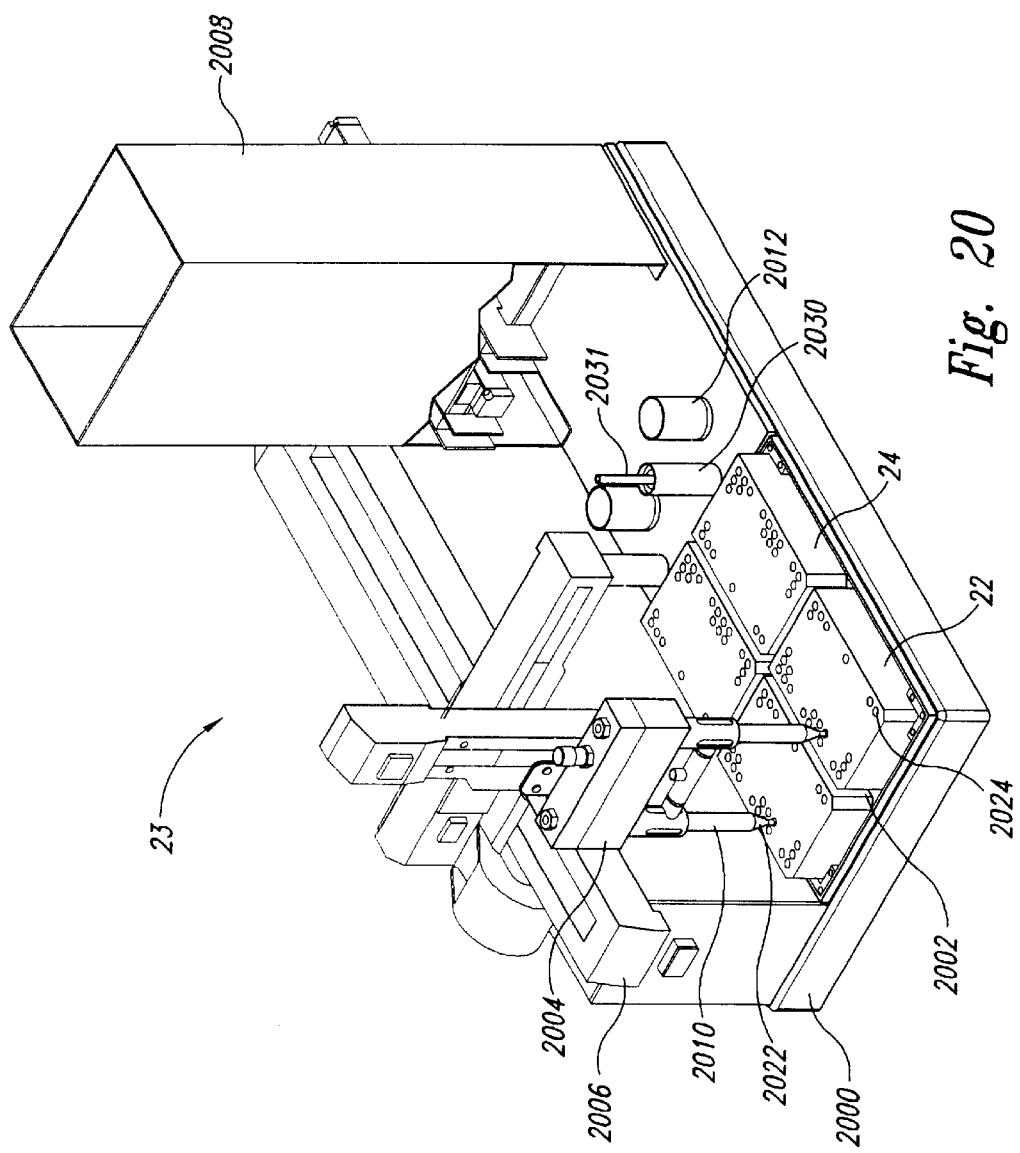
FIG. 20 is an isometric view of the fraction collection assembly of FIG. 19 shown in a collection position.

As best seen in FIG. 20, the fraction collector assembly 43 includes a frame 2000 that supports a docking station 2002 that removably receives the receiving microtiter plates 22 and 24. The fraction collector assembly 43 also includes a dispensing head 2004 that travels laterally along a rail 2006 mounted to the frame 2000 between several operating positions, discussed below.

The fraction collector assembly 43 includes a hopper 2008 that contains clean, disposable expansion chambers 2010. The fraction collector assembly 43 is configured to provide the expansion chambers 2010 from the hopper 2008 to a pickup station 2012. The pickup stations 2012 holds the expansion chambers 2010 in a substantially vertical orientation with an open top end 2020 of the expansion chamber facing upwardly. The dispensing head 2004 is movable to a position over the pickup station 2012 and movable downwardly so dispensing needles 2014 on the dispensing head 2004 extend into the expansion chambers. The dispensing head 2004 then grasps the expansion chambers 2010 and lifts them from the pickup station 2012.

Figure 21:
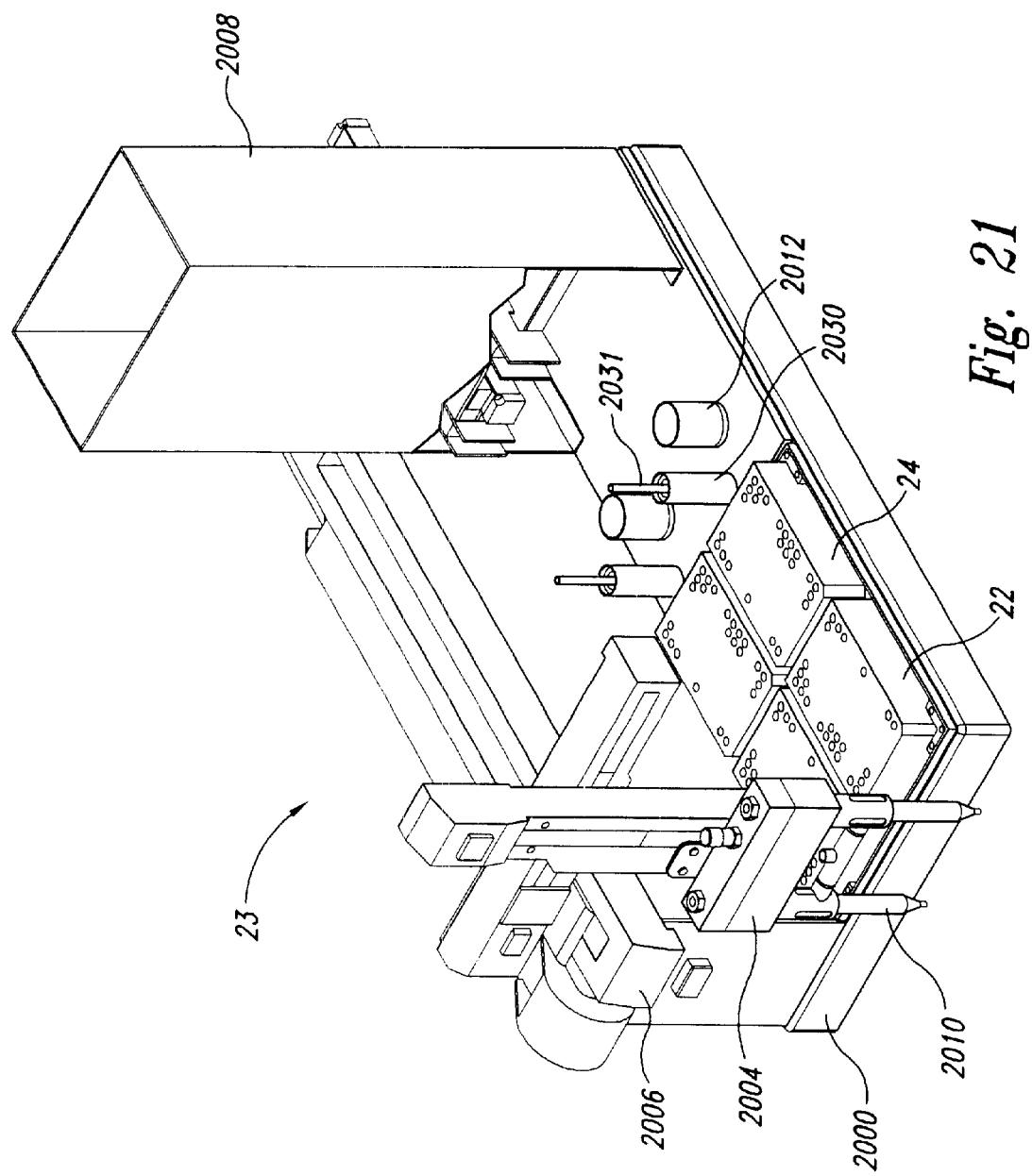
FIG. 21 is an isometric view of the fraction collection assembly of FIG. 19 shown in a chamber drop-off position.

As best seen in FIG. 21, the dispensing head 2004 moves the expansion chambers 2010 from the pickup station 2012 to a dispensing position over selected wells 2024 in the microtiter plates 22 and 24. The dispensing head 2004 is coupled to the computer controller 18 that controls the positioning of the expansion chambers 2010 over the wells 2024 so as to correspond to the well locations from which the sample was originally taken. The dispensing head 2004 moves the expansion chambers 2010 downwardly so as to extend at least partially into the selected wells 2024. Once the expansion chamber 2010 is lowered, the sample portion containing either the target or the crude is deposited from the dispensing needle 2014, into the expansion chamber 2010, and into the selected well 2024 in the microtiter plate 22 or 24.

Figure 18:
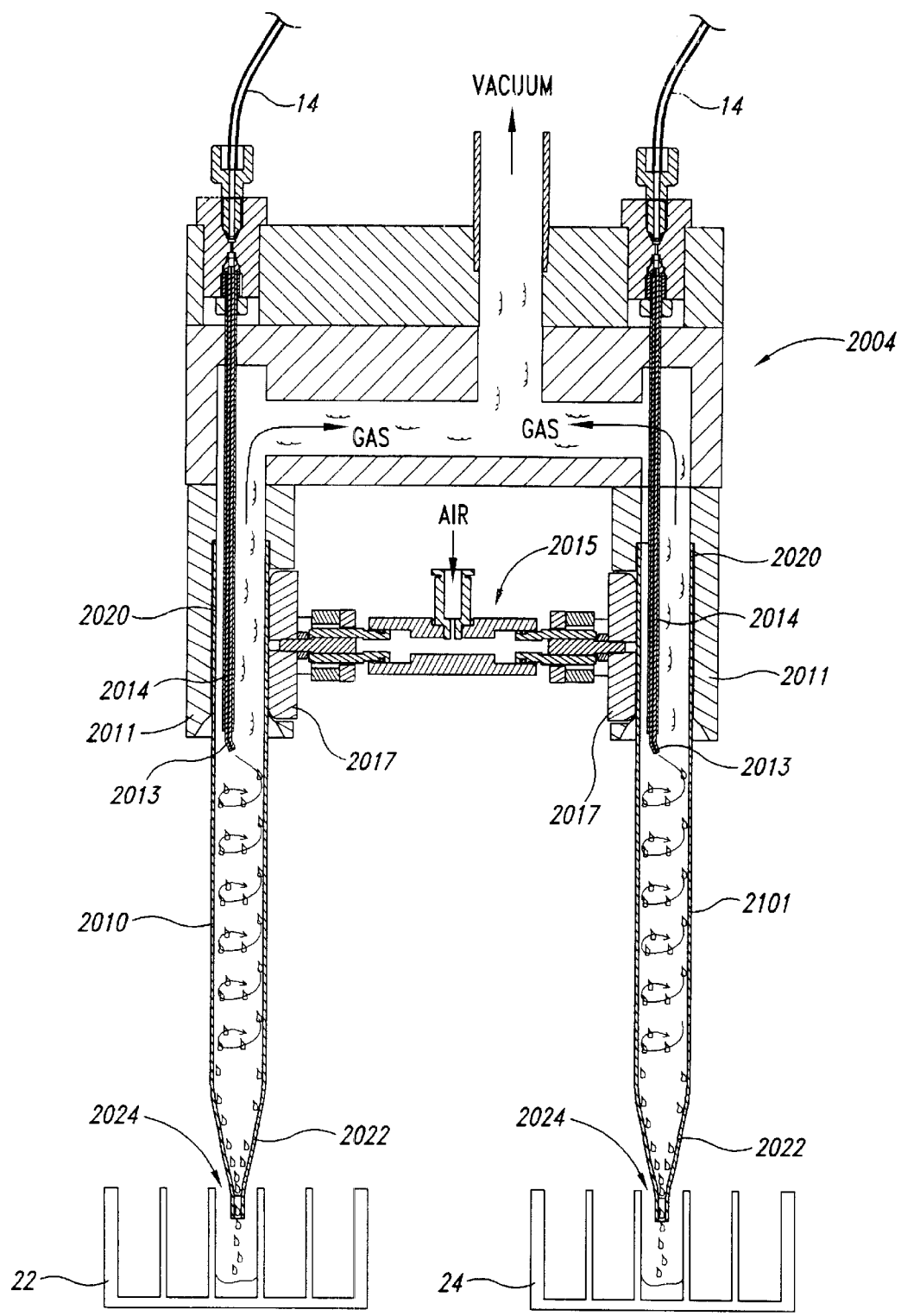
FIG. 18 is an enlarged cross-sectional view of a dispensing head and an expansion chamber from the purification system of FIG. 3, the dispensing head being shown in a dispensing position.

As best seen in FIG. 18, the dispensing head 2004 of the illustrated embodiment releasably holds two expansion chambers 2010 in tubular holding members 2011. A pneumatic gripping assembly 2015 is connected to each tubular holding member 2011 in a position to releasably engage the expansion chambers 2010. The gripping assembly 2015 includes a pair of grippers 2017 connected to pneumatic cylinders 2019. The pneumatic cylinders 2019 move the grippers 2017 relative to the tubular holding member 2011 between holding and released positions. In the holding position, each gripper 2017 presses the expansion chamber 2010 against the tubular holding member 2011, so the expansion chamber is frictionally held in the tubular holding member. In the released position, each gripper 2017 is positioned to allow the respective expansion chamber 2010 to freely move into or out of the tubular holding member 2011.

The expansion chamber 2010 is a tubular member having the open top end 2020 that is releasably engaged by the gripping assembly 2015 of the dispensing head 2004, and a tapered, open bottom end 2022. The open bottom end 2022 is positionable partially within a selected well 2024 of the microtiter plate 22 or 24. The expansion chamber's open top end 2020 is positioned so the dispensing needle 2014 extends therethrough into the expansion chamber's interior area 2028. The dispensing needle 2014 is positioned adjacent to the expansion chamber's sidewall so the needle is not coaxially aligned with the expansion chamber. The distal end 2013 of the dispensing needle 2014 is angled so as to point toward the respective expansion chamber's sidewall.

As the sample portion is dispensed from the dispensing needle 2014 into the interior area 2028 of the expansion chamber 2010, the sample portion is in an atomized state.

The atomized sample portion enters the expansion chamber 2010 through the needle's angled distal end 2013, and the distal end direct the flow toward the expansion chamber's sidewall. The atomized sample portion condenses on the expansion chamber's sidewalls as a liquid, and is directed so the condensed liquid moves along the sidewalls in a downwardly spiral direction.

The condensed, non-atomized liquid sample portion flows out of the open expansion chamber's bottom end 2022 into the selected well 2024 in the microtiter plate 22 or 24. As the atomized sample portion is being dispensed into the expansion chamber 2010, the $CO_2$ vapor exits the expansion chamber through its open top end 2020. In the illustrated embodiment, a vacuum is drawn within the expansion chamber to draw the $CO_2$ vapors out and away from the expansion chamber's open top end 2020, thereby avoiding cross-contamination between channels.

As the sample portion is condensed in the expansion chamber 2010, some of the liquid sample portion may remain in the bottom of the expansion chamber because of a capillary action at the narrow open bottom end 2022. At this point, the fraction collection valve dispenses a selected solvent into the expansion chamber to rinse it out and carry any remaining sample into the microtiter plate 22 or 24. After the sample portion has been fully dispensed, the dispensing head 2004 can provide a puff of low pressure air into the expansion chamber 2010. The air forces the remaining liquid sample out of the expansion chamber 2010 and into the well 2024.

As best seen in FIG. 21, after the sample has been dispensed into the microtiter plate 22 or 24, the dispensing head 2004 moves to a chamber drop-off off position so the expansion chambers 2010 are positioned past the edge of the frame 2000. The gripping assembly 2015 of the dispensing head 2004 moves to the released position and the expansion chambers 2010 drop into a suitable waste receptacle. In one embodiment, the expansion chambers 2010 are thrown away. In an alternate embodiment, the expansion chambers 2010 are recycled so as to be reusable.

Figure 19:
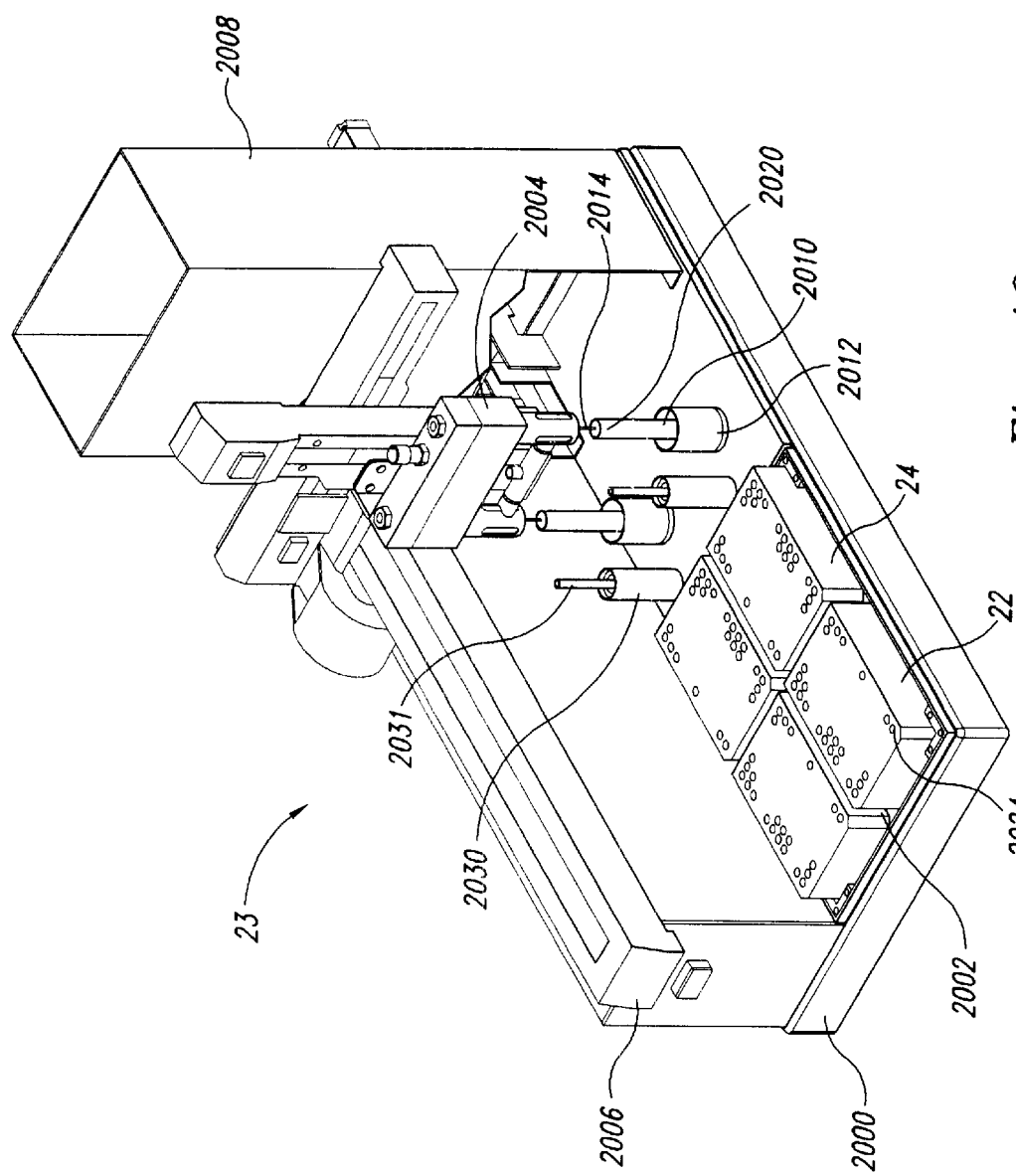
FIG. 19 is an isometric view of an automated fraction collection assembly of the purification system of FIG. 3, the assembly shown in a chamber pickup position.

After the dispensing head 2004 drops off the expansion chambers, the dispensing head moves to a needle rinse position, illustrated in FIG. 22. In this needle rinse position, the dispensing head 2004 is positioned over a pair of wash stations 2030. As seen in FIGS. 19–21, the wash stations 2030 each include a wash tube 2031 that dispenses a cleaning solvent or other solution. The wash tubes 2031 are sized and positioned so the dispensing head 2004 can lower the dispensing needles 2014 into the wash tube 2031. The wash station 1230 is then energized and dispenses cleaning fluid onto the outside of the dispensing needles 2014. The dispensing head 2004 is then raised washing the dispensing needles 2014 from the top to the bottom as they are withdrawn from the wash tube 2031. The dispensing head 2004 is then moved back to the expansion chamber pickup position, illustrated in FIG. 20, wherein new expansion chambers are picked up and ready for dispensing other sample portions into the microtiter plates 22 and 24.

The high throughput purification system 10 of the illustrative embodiment allows for relatively fast sample purification as compared to conventional purification processes. A purification run of a selected sample can be accomplished in approximately 6–8 minutes or faster. Therefore, purification of samples contained in a 96 well microtiter plate will take approximately 144–192 minutes. Purification of 4,000 samples generated in a week using sample generation techniques, discussed above, will only take in the range of 250–330.3 hours, as opposed to the 2,000 hours required to purify the 4,000 samples, using conventional purification techniques. Therefore, the high throughput purification system in accordance with the present invention allows for a significant increased speed of purification. This system also provides for collecting the purified samples directly into a microtiter plate in wells having a location address corresponding to the location address of the well in the microtiter plate from which the samples were originally drawn. Thus, the purified compounds are ready to be screened or otherwise processed. The result is a significantly increased capacity for purification that allows for a less expensive purification process.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A high through liquid chromatography column assembly configured to receive first and second packing materials and a selected sample for flow therethrough to achieve a selected chromatographic separation of the sample, the sample having a mass weight and a fluid volume, comprising:

a loading column having a first packing material and a loading chamber having a first inner diameter and first length, the loading chamber being sized to contain a volume of a first packing material with a vertical absorptive profile, the loading chamber being sized to retain a selected volume of the first packing material to spatially distribute the sample within the loading chamber to load the sample prior to chromatographic separation of the sample, the length of the loading chamber being insufficient to achieve the selected chromatographic separation of the sample as the sample passes through the loading chamber; and a separation column having a second packing material and a separation chamber therein in fluid connection with the loading chamber and being positioned to receive the sample from the loading column, the separation chamber having a second diameter smaller than the first diameter and having a second length greater that the first length, the separation chamber being sized to retain the second packing material, the second length of the separation chamber being sufficient to achieve the selected chromatographic separation of the sample as the sample passes therethrough, the separation chamber having a volume of the second packing material over a same length as the first length that is insufficient to act as a loading region for the entire selected sample.

2. The chromatography column assembly of claim 1 wherein the first diameter is two or more times greater than the second diameter.

3. The chromatography column assembly of claim 1 wherein the first length is one half or less than the second length.

4. The chromatography column assembly of claim 1 wherein the loading column has an outlet and the separation column has an inlet, the loading column and the separation column are spaced apart from each other and interconnected by a carrier tube, connected to the loading column's outlet and the separation column's inlet.

5. The chromatography column assembly of claim 1, further comprising a dilution column having a dilution chamber in fluid connection with the loading chamber.

6. The chromatography column assembly of claim 5, wherein the dilution chamber has a first inlet and outlet, the loading column has a second inlet and outlet and the separation column has a third inlet, the dilution column, the loading column, and the separation column are spaced apart from each other, the dilution column being in fluid communication with the loading chamber through a first carrier tube connected to the distribution column's first outlet and the loading column's second inlet, the loading column being in fluid communication with the separation column by a second carrier tube connected to the loading column's second outlet and the separation column's third inlet.

7. The chromatography column assembly of claim 5 wherein the dilution column, the loading column, and the separation column are spaced apart from each other, the dilution column being fluidly connected to the loading chamber by a first carrier tube, and the loading column being fluidly connected to the separation column by a second carrier tube.

8. The chromatography column assembly of claim 7 wherein the first and second carrier tubes are small bore high pressure liquid chromatography tubes.

9. The chromatography column assembly of claim 5 wherein the dilution chamber contains inert packing material therein.

10. The chromatography column assembly of claim 1 wherein the loading column and the separation column are spaced apart from each other and are in fluid communication through a carrier tube extending therebetween.

11. The chromatography column assembly of claim 1 wherein the loading column and the separation column are integrally connected to each other.

12. The chromatography column assembly of claim 1, Teflon coating portions of the first and second columns that come in contact with fluid.

13. The chromatography column assembly of claim 1, further comprising a dilution column having a dilution chamber in fluid communication with the loading chamber, a portion of the dilution column being positioned in the loading chamber, the dilution chamber and the loading chamber being separated by a frit.

14. The chromatography column assembly of claim 13 wherein the frit is positionable in the loading chamber and sandwiched between the dilution column and the first packing material in the loading chamber.

15. The chromatography column assembly of claim 1, further comprising a dilution column having a dilution chamber in fluid connection with the loading chamber, a bottom end of the dilution column being securely connected to a top end of the loading column.

16. The chromatography column assembly of claim 15 wherein a frit is sandwiched between the dilution column and the loading column.

17. The chromatography column assembly of claim 1 wherein the separation chamber has a substantially constant cross sectional area along the second length.

18. The chromatography column assembly of claim 1 wherein the separation chamber has first and second end portions, the first and portion being closest to the loading column, the second diameter being at the first end portion, and the separation chamber having a third diameter at the second end portion smaller than the second diameter.

19. The chromatography column assembly of claim 1 wherein the separation chamber has a truncated conical shape.

20. A system for liquid chromatography, comprising a carrier tube with inlet and outlet portions, and two columns; the first column being coupled to the inlet portion of the carrier tube and being about ½ or less than the length of the second column and having internal diameter approximately two or more times the internal diameter of the second column, and the second column connected to the outlet portion of the carrier tube.

21. The system of claim 20, further including a dilution chamber adjacent to and prior of the first column, said dilution chamber having a selected geometric interior volume.

22. The system of claim 21 wherein the first and second columns are integrally connected to each other.

23. The system of claim 20 wherein the first and second columns are integrally connected to each other.

24. The system of claim 20, further including Teflon coating portions of the first and second columns that come in contact with fluid.

25. A chromatographic column, comprising first and second column portions, the first column portion having a loading chamber with a first inner diameter and first length, the second column portion having a separating chamber with a second inner diameter and second length, the first inner diameter being approximately two times greater than the second inner diameter and the first length being approximately ½ or less than the second length.

26. The column of claim 25 wherein the first inner diameter is at least approximately two times greater than the second inner diameter.

27. The column of claim 26 wherein the first length is approximately equal to or less than one-half of the second length.

28. The column of claim 25 wherein the first length is approximately equal to or less than one-half of the second length.

29. The column of claim 25 wherein the first and second column portions contains a solid phase material.

30. The column of claim 25 further comprising a dilution chamber adjacent to the first chamber with the first chamber being between the dilution chamber and the second chamber.

31. The column of claim 25 wherein the first column portion has a funnel-shaped transition portion connected to the second column portion.

32. The column of claim 25 wherein the first column portion is releasably connected to the second column portion.

33. The column of claim 25 wherein the first column portion is integrally connected to the second column portion.

34. The column of claim 25 wherein the second chamber portion is a tapered chamber that tapers inwardly as the second column portion extends away from the first column portion.

* * * * *